United States Patent
Otts et al.

(10) Patent No.: US 11,197,752 B2
(45) Date of Patent: Dec. 14, 2021

(54) SITU FILLING AND SEALING OF ELECTROWETTING INTRAOCULAR LENSES

(71) Applicant: Verily Life Sciences LLC, Mountain View, CA (US)

(72) Inventors: Daniel Otts, Pleasanton, CA (US); Stein Kuiper, South San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 846 days.

(21) Appl. No.: 15/945,880

(22) Filed: Apr. 5, 2018

(65) Prior Publication Data

US 2018/0318068 A1 Nov. 8, 2018

Related U.S. Application Data

(60) Provisional application No. 62/501,834, filed on May 5, 2017.

(51) Int. Cl.
*A61F 2/16* (2006.01)
*A61L 27/50* (2006.01)
(Continued)

(52) U.S. Cl.
CPC ............ *A61F 2/1635* (2013.01); *A61L 27/18* (2013.01); *A61L 27/50* (2013.01);
(Continued)

(58) Field of Classification Search
CPC .... A61F 2/1613; A61F 2/1618; A61F 2/1624; A61F 2/1627; A61F 2/1635; A61F 2250/0003; A61F 2250/0013
See application file for complete search history.

(56) References Cited

U.S. PATENT DOCUMENTS

| 4,585,457 | A | | 4/1986 | Kalb | |
|---|---|---|---|---|---|
| 4,685,921 | A | * | 8/1987 | Peyman | A61F 2/1613 623/6.13 |

(Continued)

FOREIGN PATENT DOCUMENTS

| WO | 2005088388 A1 | 9/2005 |
|---|---|---|
| WO | 2007051171 A2 | 5/2007 |

(Continued)

OTHER PUBLICATIONS

International Search Report and Written Opinion of International Application No. PCT/US2018/026714 dated Jun. 28, 2018.

(Continued)

*Primary Examiner* — William H Matthews
(74) *Attorney, Agent, or Firm* — McDonnell Boehnen Hulbert & Berghoff LLP

(57) ABSTRACT

An eye-implantable electrowetting lens can be operated to control an overall optical power of an eye in which the device is implanted. A lens chamber of the electrowetting lens contains first and second fluids that are immiscible with each other and have different refractive indexes. By applying a voltage to electrodes of the lens, the optical power of the lens can be controlled by affecting the geometry of the interface between the fluids. When the electrowetting lens is inserted into the eye, the lens chamber may contain only one of the first and second fluids. The other fluid can be added after insertion through a needle, a tube, or some other means. Having only one of the first and second fluids in the lens chamber during insertion of the lens can prevent fouling of internal surfaces due to folding or other manipulation of the lens during the insertion process.

20 Claims, 9 Drawing Sheets

(51) Int. Cl.
*A61L 27/18* (2006.01)
*G02C 7/08* (2006.01)
*G02B 26/00* (2006.01)

(52) U.S. Cl.
CPC .............. *A61F 2210/0014* (2013.01); *A61F 2250/0001* (2013.01); *A61F 2250/0003* (2013.01); *A61F 2250/0015* (2013.01); *A61F 2250/0053* (2013.01); *G02B 26/005* (2013.01); *G02C 7/085* (2013.01)

(56) References Cited

U.S. PATENT DOCUMENTS

| | | | |
|---|---|---|---|
| 7,522,345 | B2 | 4/2009 | Oh et al. |
| 8,382,280 | B2 | 2/2013 | Gupta et al. |
| 8,390,934 | B2 | 3/2013 | Kong et al. |
| 8,390,939 | B2 | 3/2013 | Henriksen et al. |
| 8,460,376 | B2 | 6/2013 | Donitzky et al. |
| 8,665,526 | B2 | 3/2014 | Pugh et al. |
| 8,792,173 | B2 | 7/2014 | Bae et al. |
| 2004/0010310 | A1* | 1/2004 | Peyman ............ A61F 2/16 623/6.12 |
| 2007/0153405 | A1* | 7/2007 | Kuiper ............ G02B 26/005 359/846 |
| 2008/0137213 | A1 | 6/2008 | Kuiper et al. |
| 2009/0005865 | A1* | 1/2009 | Smiley ............ A61F 2/1635 623/6.13 |
| 2012/0113525 | A1 | 5/2012 | Kong et al. |
| 2013/0229618 | A1 | 9/2013 | Otts et al. |
| 2013/0258277 | A1 | 10/2013 | Pugh et al. |
| 2014/0253870 | A1 | 9/2014 | Jiang et al. |
| 2015/0043085 | A1 | 2/2015 | Tsuji |

FOREIGN PATENT DOCUMENTS

| | | |
|---|---|---|
| WO | 2009015234 A2 | 1/2009 |
| WO | 2011137191 A1 | 11/2011 |
| WO | 2014193953 A2 | 4/2014 |

OTHER PUBLICATIONS

Mugele et al., "Electrowetting: from basics to applications", Topical Review, Journal of Physics: Condensed Matter, Published Jul. 1, 2005.

B. Berge, "Liquid Lens Technology: Principle Of Electrowetting Based Lenses And Applications To Imaging", IEEE, 2005, pp. 227-230.

Lu et al., "Tunable dielectric liquid lens on flexible substrate", Applied Physics Letters 103, 2013.

Mallin, "Flexible Membrane Liquid Lens", Optics & Optoelectronics, 2011 NNIN REU Research Accomplishments.

Li et al., "Fabrication and Characterization of Flexible Electrowetting on Dielectrics (EWOD) Microlens", NIH Author Manuscript, 2014, 432-441.

Li et al., "Electrowetting-driven variable-foxus microlens on flexible surfaces", Applied Physics Letters 100, 2012.

Bae et al., "Unique Fluid Ensemble including Silicone Oil for the Application of Optical Liquid Lens", Bull. Korean Chem. Soc. 2008, vol. 29, No. 4, pp. 731-735.

\* cited by examiner

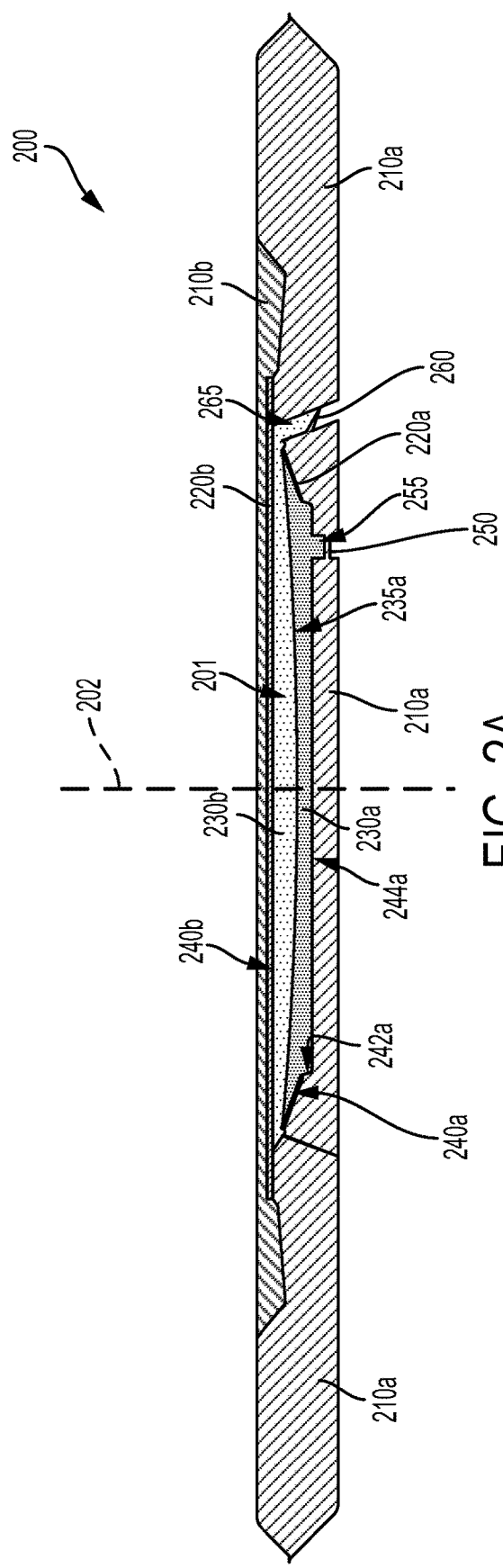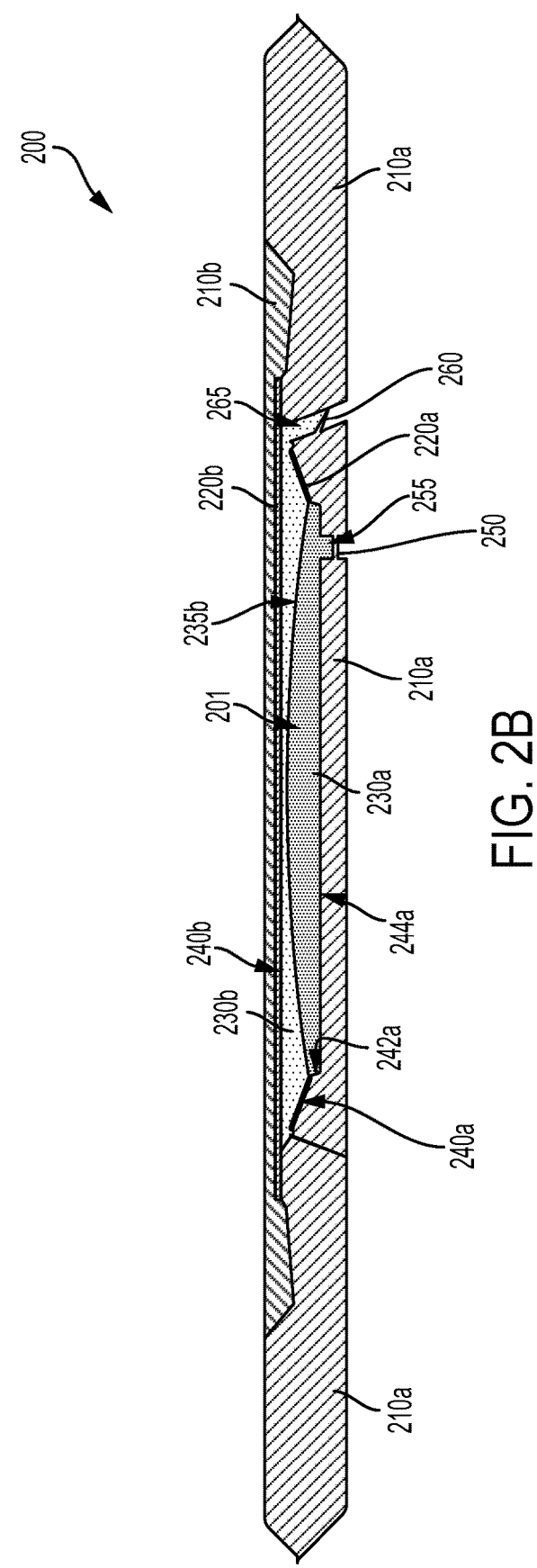

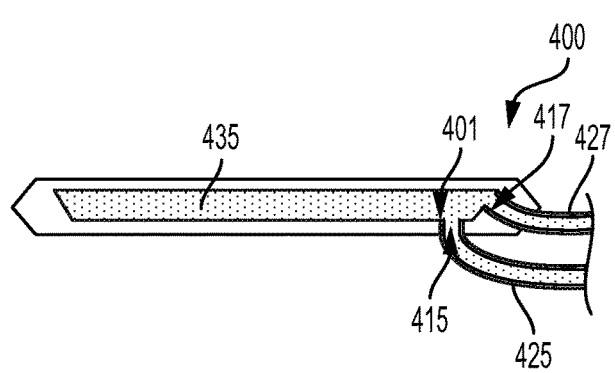 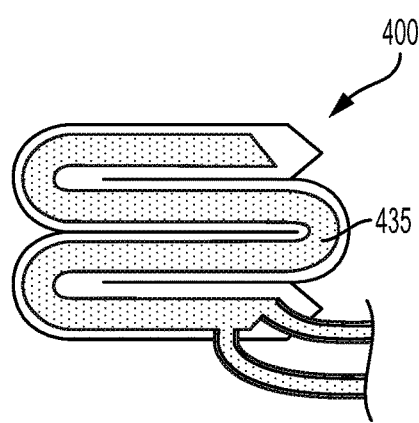
FIG. 4A      FIG. 4B
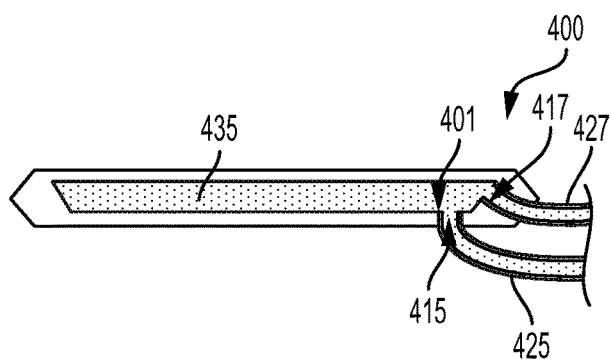
FIG. 4C

SITU FILLING AND SEALING OF ELECTROWETTING INTRAOCULAR LENSES

CROSS-REFERENCE TO RELATED APPLICATION

This application claims priority to U.S. Provisional Patent Application No. 62/501,834, filed May 5, 2017, which is incorporated herein by reference.

BACKGROUND

Unless otherwise indicated herein, the materials described in this section are not prior art to the claims in this application and are not admitted to be prior art by inclusion in this section Devices can be provided on the surface of the eye and/or within the eye to provide a variety of functions. In some examples, these functions can include functions to improve the ability of a person to view their environment (e.g., to provide an optical correction, to stimulate the retina directly) and/or to present additional visual information to the person (e.g., to present a heads up display or other indications to the person). Additionally or alternatively, these functions can include detecting a property of the body of a person (e.g., a blood glucose level, a concentration of an ion in the blood, a desired optical power of the eye) via the eye, e.g., by detecting forces, concentrations of analytes, electrical fields, or other properties related to the property of interest. Such functions can be provided by an intraocular device implanted within the eye (e.g., a retinal implant configured to stimulate the retina to restore vision, a device implanted within the lens capsule to provide a static and/or controllable optical power to the eye).

Such an eye-implantable device could include an electronically adjustable lens to provide a controllable amount of optical power to the eye. Such an electronically adjustable lens could be provided to correct for presbyopia. Presbyopia is a reduction in the eye's ability to naturally adjust its focal length, e.g., by deforming the crystalline lens of the eye. An electronically actuated lens could include a lens chamber that contains two or more immiscible fluids whose geometry within the lens chamber can be electronically controlled in order to control an overall optical power of the lens.

SUMMARY

Some embodiments of the present disclosure provide an eye-implantable device that includes an electrowetting lens. The electrowetting lens includes: (i) a lens chamber; (ii) a first fluid disposed in the lens chamber; (iii) a first electrode that is disposed on an internal surface of the lens chamber in contact with the first fluid; (iv) a second electrode that is disposed on an internal surface of the lens chamber in contact with the first fluid and that includes a dielectric coating; and (v) a septum that blocks a fluid pathway into the lens chamber from outside of the eye-implantable device. The septum can be penetrated so that a second fluid may be introduced into the lens chamber through the fluid pathway from outside of the eye-implantable device.

Some embodiments of the present disclosure provide an eye-implantable device that includes an electrowetting lens. The electrowetting lens includes: (i) a lens chamber; (ii) a first fluid disposed in the lens chamber; (iii) a first electrode that is disposed on an internal surface of the lens chamber in contact with the first fluid; (iv) a second electrode that is disposed on an internal surface of the lens chamber in contact with the first fluid and that includes a dielectric coating; and (v) a tube that protrudes from the eye-implantable device, that provides at least a portion of a fluid pathway into the lens chamber from outside of the eye-implantable device, and that includes a crimpable portion. A second fluid can be introduced into the lens chamber through the tube from outside of the eye-implantable device. Further, crimping the crimpable portion of the tube can inhibit fluid flow out of the eye-implantable device via the tube.

Some embodiments of the present disclosure provide a method including: (i) forming an incision through a cornea of an eye; and (ii) inserting an eye-implantable device into the eye through the incision. The eye-implantable device includes an electrowetting lens. The electrowetting lens includes: (a) a lens chamber; (b) a first fluid disposed in the lens chamber; (c) a first electrode that is disposed on an internal surface of the lens chamber in contact with the first fluid; (d) a second electrode that is disposed on an internal surface of the lens chamber in contact with the first fluid and that includes a dielectric coating; and (e) a septum that blocks a fluid pathway into the lens chamber from outside of the eye-implantable device. The method further includes: (iii) placing the eye-implantable device at a specified location within the eye; (iv) piercing the septum of the eye-implantable device with a needle; and (v) introducing a second fluid into a lens chamber via the needle such that the second electrode is in contact with at least one of the first fluid or the second fluid. The second fluid is immiscible with the first fluid and a refractive index of the second fluid differs from a refractive index of the first fluid.

Some embodiments of the present disclosure provide a method including: (i) forming an incision through a cornea of an eye; (ii) inserting an eye-implantable device into the eye through the incision. The eye-implantable device includes an electrowetting lens. The electrowetting lens includes: (a) a lens chamber; (b) a first fluid disposed in the lens chamber; (c) a first electrode that is disposed on an internal surface of the lens chamber in contact with the first fluid; (d) a second electrode that is disposed on an internal surface of the lens chamber in contact with the first fluid and that includes a dielectric coating; and (e) a tube that protrudes from the eye-implantable device and that provides at least a portion of a fluid pathway into the lens chamber from outside of the eye-implantable device. The method further includes: (iii) placing the eye-implantable device at a specified location within the eye; (iv) introducing a second fluid into the lens chamber via the tube such that the second electrode is in contact with at least one of the first fluid or the second fluid; and (v) cutting the tube. The second fluid is immiscible with the first fluid and a refractive index of the second fluid differs from a refractive index of the first fluid.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2A is a side cross-section view of an example eye-implantable device.

FIG. 2B is a side cross-section view of an example eye-implantable device shown in FIG. 2A.

FIG. 4A is a side cross-section view of an example eye-implantable device.

FIG. 4B is a side cross-section view of the example eye-implantable device of FIG. 4A after being folded up.

FIG. 4C is a side cross-section view of the example eye-implantable device of FIG. 4B after being unfolded.

DETAILED DESCRIPTION

Figure 1A:
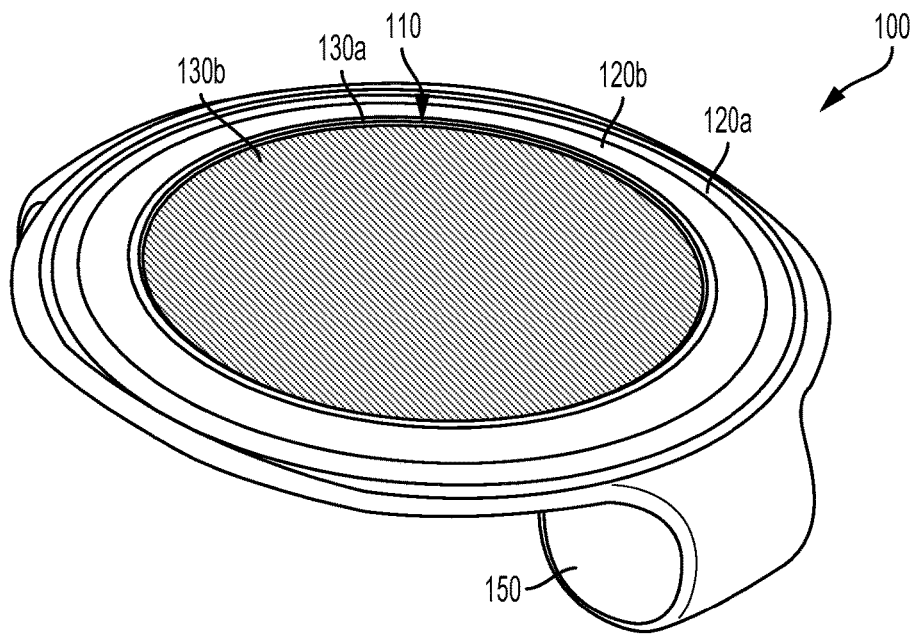
FIG. 1A is a perspective view of an example eye-implantable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

Implantable devices could be located within an eye of a person to provide a static or adjustable optical power to the eye. Such a static or adjustable optical power could be provided to correct a lack or loss of optical power and/or accommodation in the eye, e.g., to correct for presbyopia, myopia, hyperopia, astigmatism, injury or damage to the eye, removal of the crystalline lens of the eye, or to correct for some other condition of the eye. Such implantable devices could be located within the lens capsule, within the anterior chamber, within the fibrous wall of the eye, proximate to the retina, or in some other location(s) of the eye according to an application. Such an eye-implantable device could include an electronically adjustable lens to provide a controllable amount of optical power to the eye. An electronically adjustable lens could include an electrowetting lens that includes two or more immiscible fluids whose geometry within the electrowetting lens can be electronically controlled (e.g., by applying an electrical voltage to two or more electrodes of the lens) in order to control an overall optical power of the electrowetting lens. Such an adjustable lens could be configured in some other way to control an overall optical power of the lens, e.g., by pumping an amount of one or more immiscible fluids into or out of a lens chamber (e.g., via electrowetting or some other process).

To facilitate implantation of such an eye-implantable device, it can be beneficial for the device to be flexible. Such a flexible device could be bent, folded, or otherwise manipulated to permit implantation. The device could subsequently be unfolded or otherwise manipulated into a flat or otherwise operational state. For example, the eye-implantable device could be rolled up or folded (e.g., in half, in thirds) to facilitate insertion into the eye by way of an incision that is smaller than the unfolded size of the device (e.g., via an incision that is smaller than an unfolded diameter of a lens of the eye-implantable device). Such flexibility could improve biocompatibility, speed or otherwise improve the process of implantation, permit detection of forces applied to the device, or could provide some other benefit.

However, where such a device includes an electrowetting or otherwise configured lens that contains two or more immiscible fluids, folding or otherwise manipulating the lens can cause the immiscible fluids within the lens to disperse into each other (e.g., the fluids could form an emulsion, a suspension, or some other mixture wherein droplets of one of the fluids are dispersed into the other fluid and/or vice versa), to contact and wet surfaces that they should not come into contact with, or to result in other deleterious effects. For example, when an oil (or other nonpolar fluid) of a lens comes into contact with an interior surface of the lens that is intended to be in contact with saline (or with some other polar fluid) of the lens, the oil can wet and/or foul the interior surface. This wetting and/or fouling can result in decreased clarity or some other deleterious effect on the optical properties and/or functioning of the lens.

To reduce such unwanted effects, one or more fluids (e.g., an oil or other nonpolar fluid) could be omitted from the lens. Such a lens could be inserted into the eye and/or otherwise manipulated prior to introduction of the omitted fluid(s) into the lens. Such an omitted fluid could be introduced into the lens after the insertion into the eye or other manipulations of the lens are complete. For example, the omitted fluid could be introduced into the lens after the lens has been inserted into the eye and after the lens has been unfolded, but before the lens is positioned at a target location within the eye (e.g., within a lens capsule of the eye). One or more fluids could be introduced into such a lens and/or removed from the lens (e.g., to maintain a total volume of fluid within the lens at a specified level, to rinse bubbles out of the lens chamber).

Such fluid(s) could be added or removed from the lens chamber of a lens in a variety of ways. In some examples, the lens and/or an eye-implantable device that includes the lens could include a septum or other feature that can be pierced by a needle. The omitted fluid could then be introduced into the lens chamber of the lens via the needle. Additionally or alternatively, some other fluid (e.g., saline or some other polar fluid) could be extracted from the lens chamber via the needle or via another needle or via some other means. In further examples, one or more tubes (e.g., flexible tubes composed of a silicone material) could be connected to the lens chamber of the lens. Such tubes could extend back through an incision via which the lens is inserted into an eye; following such insertion and/or other manipulations of the lens, the tube(s) could be used to introduce an oil or other fluid into the lens, to receive surplus fluid from the lens, or to facilitate some other operations. Such a tube could then be cut (e.g., by a sharp edge, by application of a tension along the tube, by application of light or acoustic energy, or by some other means) and/or sealed and the cut-off portion of the tube could be removed from the eye. Other means or methods for introducing a fluid into a lens that has been inserted into an eye are contemplated.

Such eye-implantable devices could include electronics, antennas, voltage regulators, batteries, photovoltaic cells, sensors, or other elements to facilitate operations of the device, e.g., to provide a controllable optical power to an eye. Such eye-implantable devices could receive, from outside of the eye, radio frequency, optical, infrared, acoustic, or other forms of power to power the operations of the device, e.g., from a contact lens, eyeglasses, a head-mountable device, or some other source. The eye-implantable device could receive wireless transmissions to specify an amount of optical power to provide, via controlling the optical power of the lens, to the eye, could operate a sensor to detect a physical variable (e.g., an accommodation force exerted by ciliary muscles of the eye) to specify the amount of optical power to provide, or the eye-implantable device could use some additional or alternative source of information or commands to determine an amount of optical power to provide to an eye.

II. EXAMPLE EYE-IMPLANTABLE DEVICE

An eye-implantable device (e.g., an intraocular lens, or IOL) can include electronics and an electronically adjustable lens that are operable to provide a controllable optical power (e.g., a controllable diopter, focal length, or other form of optical power or refractive property) to an eye in which the device is implanted. Such an eye-implantable device could include haptics or other formed features, or be formed according to a particular shape, such that the eye-implantable device can be implanted in or at a particular location within an eye, e.g., within the lens capsule of the eye following removal of the crystalline lens, within the anterior chamber of the eye, within the posterior chamber of the eye, along an optical axis of the eye. A controller, battery, antenna, sensors, or other elements can be provided to power the device, to determine a specified amount of optical power to provide to the eye (e.g., based on a sensor output, based on a received wireless command), and to operate the electronically adjustable lens to provide such a specified optical power by applying a voltage, current, or other electrical signal to the electronically adjustable lens. In some examples, the electronically adjustable lens could be an electrowetting lens.

Note that, while reference is made throughout this application to electrowetting lenses of eye-implantable devices, the embodiments provided herein could be applied to other applications. For example, filling features could be provided as part of a flexible lens of an eye-implantable device that is configured to control an optical power of the lens via some process other than or in addition to electrowetting. Such a device could be configured to pump one or more immiscible fluids into or out of a lens chamber of a lens using a piezo actuator, a electrowetting actuator, a shape-memory actuator, or other actuator to pump the one or more fluids into or out of the lens chamber.

Figure 1B:
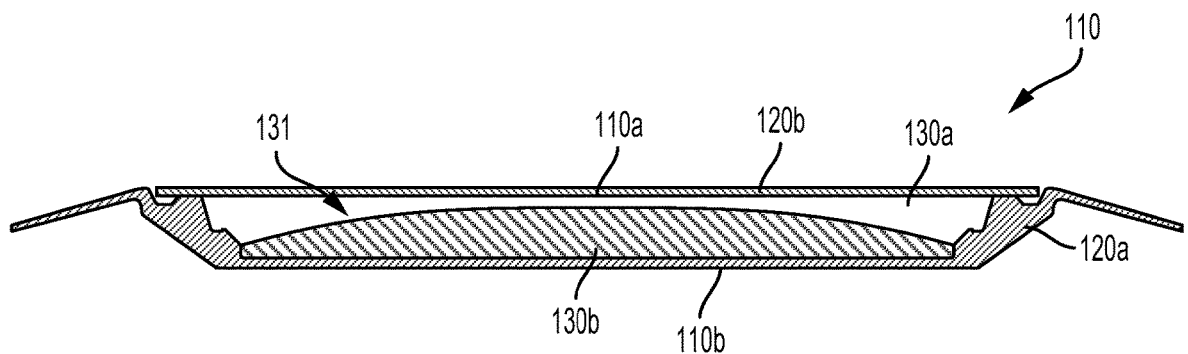
FIG. 1B is a side cross-section view of an electrowetting lens of the example eye-implantable device shown in FIG. 1A.

FIG. 1A is a bottom view of an example eye-implantable device 100. FIG. 1B is a cross-sectional view of an electrowetting lens 110 of the example eye-implantable device 100 shown in FIG. 1A. It is noted that relative dimensions in FIGS. 1A and 1B are not necessarily to scale, but have been rendered for purposes of explanation only in describing the arrangement of the example eye-implantable device 100 and electrowetting lens 110 thereof. The eye-implantable device 100 includes electronics 150 configured to operate the electrowetting lens 110 to provide a controllable optical power and to provide other operations of the eye-implantable device 100. The electronics 150 may include controllers, voltage regulators, antennas, photovoltaic cells, sensors, electrodes, transmitters, receivers, batteries, or other components. The electronics 150 may be configured to receive and/or store wireless energy to power the device 100 (e.g., visible light energy, infrared light energy, radio frequency electromagnetic energy, acoustic energy), to communicate with external devices or systems (e.g., to receive program updates, to receive a commanded optical power level), to detect one or more physical variables (e.g., a light level, a pupil diameter, an intraocular pressure, a voltage related to activity of muscles of the eye, a force exerted by ciliary muscles of the eye, a concentration of one or more substances in the eye) that may be used to determine an optical power to provide or that may be used in some other way, to operate the electrowetting lens 110, or to facilitate some other applications of the device 100.

The electrowetting lens 110 and/or other elements of the eye-implantable device 100 may be formed of one or more polymeric materials. The polymeric materials can include substantially transparent materials to allow incident light to be transmitted to the retina of the eye through the electrowetting lens 110 of the eye-implantable device 100. The polymeric materials can include biocompatible materials similar to those employed to form implants, vision correction lenses, IOLs, or other implantable devices, such as polyethylene terephthalate ("PET"), polymethyl methacrylate ("PMMA"), silicone hydrogels, rigid, gas-permeable polymeric materials, barrier materials that block diffusion of gases or other substances, combinations of these, etc. The polymeric materials could include flexible and/or foldable water-permeable materials. For example, the polymeric material could include a copolymer comprising 2-phenylethyl acrylate units and 2-phenylethyl methacrylate units. Units of a polymer or copolymer could be cross-linked by an applicable cross-linking agent or unit, e.g., by 1,4-butanediol diacrylate units, 1,6-hexanediol diacrylate units, or some other crosslinking agent or combination of such agents. Such flexible and/or foldable materials may be included in the construction of the device 100 to permit the device 100 to be rolled, folded, or otherwise manipulated such that the device 100 may be inserted through an incision that is smaller than, e.g., the diameter of the unrolled or un-folded electrowetting lens 110. The eye-implantable device 100 may include coating materials disposed on one or more external or internal surfaces of the device, e.g., to improve a biocompatibility of the device, to control a surface energy of an internal surface of the electrowetting lens (e.g., to encourage or prevent wetting of a surface that at least partially encloses a lens chamber by one or more fluids within the lens chamber), to prevent passage of ions or other substances, or to provide some other benefit.

The electrowetting lens 110 includes a lens chamber 131 in which are disposed a first fluid 130a and a second fluid 130b. The lens chamber 131 is formed from first 120a and second 120b elements formed, respectively, as a cup and a flat lid. At least a portion of the first 120a and/or second 120b elements of the electrowetting lens 110 could be formed from a polymeric material (e.g., one of the polymeric materials listed elsewhere herein) that is permeable to water in aqueous humor of an eye (e.g., from a copolymer comprising 2-phenylethyl acrylate units and 2-phenylethyl methacrylate units cross-linked by 1,4-butanediol diacrylate units). Such a water-permeable polymeric material, or other polymeric or non-polymeric materials of the electrowetting lens 110, could be flexible such that the electrowetting lens 110 can be rolled, folded, or otherwise manipulated, e.g., to facilitate insertion through an incision in an eye. Additionally or alternatively, one or more sealant materials (e.g., a sealant material used to adhere the first element 120a to the second element 120b) of the electrowetting lens 110 could be permeable to water in aqueous humor of an eye.

Note that the illustrated first 120a and second 120b elements of the chamber 131 of the electrowetting lens 110 are intended as non-limiting example embodiments. For example, an electrowetting lens and/or a lens chamber thereof as described herein could be constructed from and/or formed more or fewer elements (e.g., from a front element, a rear element, and an annular element) than the two shown and/or could be constructed from elements configured differently from the elements 120a, 120b illustrated here. Different elements of an electrowetting lens could be composed of the same material (e.g., the elements 120a, 120b of the electrowetting lens 110 could both be composed of a copolymer comprising 2-phenylethyl acrylate units and 2-phenylethyl methacrylate units). Alternatively, elements of an electrowetting lens could be composed of respective different materials (e.g., the first element 120a could be composed of a copolymer comprising 2-phenylethyl acrylate units and 2-phenylethyl methacrylate units and the second element 120b could be composed of polyethylene terephthalate).

The first 130a and second 130b fluid are immiscible (e.g., the first fluid 130a could be saline or some other aqueous fluid and the second fluid 130b could be an oil or some other nonpolar fluid) and differ with respect to refractive index. Thus, a surface of contact between the first 130a and second 130b fluids (e.g., a convex shape, as shown in FIG. 1B) could provide an optical power (e.g., a diopter, a nonzero focal length) related to the difference in the refractive indices of the fluids 130a, 130b and the shape of the surface of contact.

The electrowetting lens 110 further includes at least two electrodes (not shown) disposed on respective internal surfaces of elements that form the lens chamber 131. Voltages, currents, or other electrical signals can be applied to the at least two electrodes to electronically control the shape of the first 130a and second 130b fluids (e.g., to control a shape of a contact surface between the two fluids 130a, 130b) in order to control an optical power of the electrowetting lens 110. In order to allow the electrowetting lens 110 to be flexed, folded, rolled, or otherwise manipulated during implantation while retaining the functionality of the lens, the electrodes could be composed of gold, aluminum, silver nanowires, or some other material or coating that can be flexed and maintain an overall level of electrical conductivity across the area of the electrodes. Such materials could be applied mechanically (e.g., as a foil) or via some other process (e.g., via sputtering, CVD, PVD, application as a solution followed by evaporation of a solvent of the solution).

One of the first 130a or second 130b fluid may include an aqueous solution. Such an aqueous solution may be electrically conductive, e.g., to facilitate transmission of electrical voltages or currents through the aqueous solution in order to control the shape of the interface between the aqueous solution and another fluid of the electrowetting lens 110. In some examples, the aqueous solution may be substantially isotonic relative to the aqueous humor of an eye into which the eye-implantable device 100 is implanted. The aqueous solution could have an osmolality corresponding to the osmolality of the aqueous humor such that, if the lens chamber is permeable to water in the aqueous humor, a small or substantially zero amount of net water flow occurs between the aqueous solution within the lens chamber and the aqueous humor of the eye. This could include the aqueous solution having an osmolality between 298 milliosmoles per kilogram and 310 milliosmoles per kilogram, or an osmolality between 300 milliosmoles per kilogram and 308 milliosmoles per kilogram, or an osmolality between 302 milliosmoles per kilogram and 306 milliosmoles per kilogram, or an osmolality between 303 milliosmoles per kilogram and 305 milliosmoles per kilogram.

The overall optical power provided by the eye-implantable device 100 and/or the electrowetting lens 110 (e.g., to an eye in which the device 100 is implanted) could be related to the geometry, refractive index, or other properties of elements of the eye-implantable device 100. As noted above, this could include the shape of a contact surface between the first 130a and second 130b fluids within the lens chamber 131 and the refractive indices of the fluids 130a, 130b.

Other elements of the eye-implantable device 100 could provide a static and/or controllable optical power. For example, the front and/or rear surfaces of the electrowetting lens 110 could have curved surfaces to provide an optical power related to a change in refractive index between materials on either side of those surfaces (e.g., between a polymeric material of the first 120a and/or second 120b elements and aqueous humor of an eye, or between the polymeric material and one of the first 130a or second 130b fluids).

Components of the eye-implantable device 100 and/or electrowetting lens 110 (e.g., the first 120a or second 120b elements forming the lens chamber 131) can be formed to have a curved shape in a variety of ways. For example, techniques similar to those employed to form vision-correction contact lenses and/or intraocular lenses, such as heat molding, injection molding, spin casting, etc. can be employed to form polymeric materials into components of the eye-implantable device 100. Further, an eye-implantable device as described herein could have a different shape from that of the illustrated eye-implantable device 100. For example, an eye-implantable device could include haptics or other formed elements to maintain the eye-implantable device at a particular location within an eye (e.g., within a lens capsule of an eye), to detect accommodation forces exerted by ciliary muscles of an eye, or to provide some other benefit.

Figure 1C:
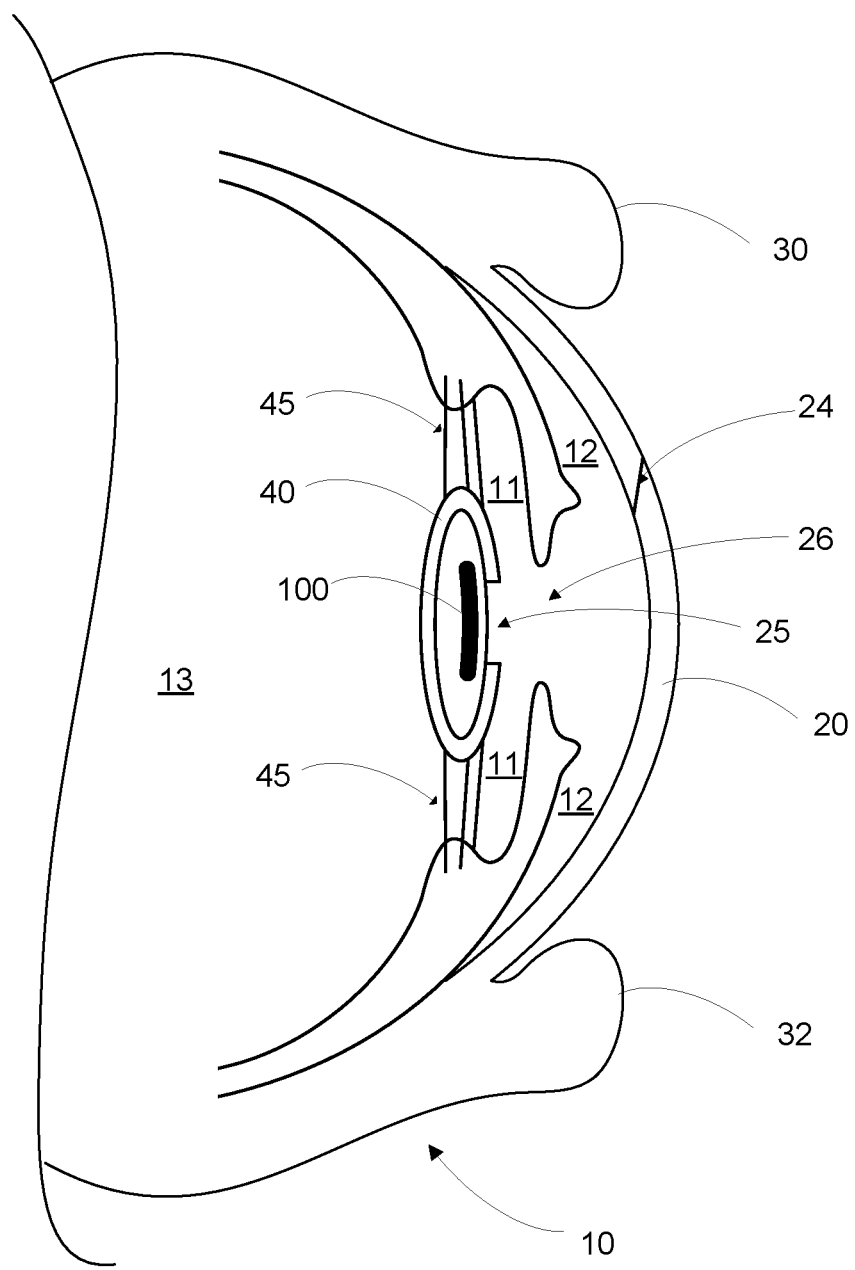
FIG. 1C is a side cross-section view of the example eye-implantable device shown in FIGS. 1A and 1B located within an eye.

FIG. 1C is a side cross-section view of the example eye-implantable device 100 while implanted within an eye 10. The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception.

The light received by the retina is transmitted, in the unaltered eye, through the crystalline lens, being refracted by the lens such that light received from the environment arrives in focus at the retina. The crystalline lens is located within the lens capsule 40 of the eye, which is connected, via the zonules 45, to accommodation muscles (e.g., ciliary muscles) and other elements of the eye. Accommodation forces transmitted through the zonules (e.g., forces generated by the accommodation muscles, forces generated by intrinsic elasticity of the zonules, or forces generated by other sources) act, in the eye, to deform the crystalline lens within the lens capsule 40, controlling the optical power provided by the crystalline lens.

As shown in FIG. 1C, the crystalline lens of the eye 10 has been removed and the eye-implantable device 100 has been surgically emplaced within the lens capsule 40 such that light received by the retina is transmitted through the electrowetting lens 110 of the eye-implantable device 100, being refracted by the electrowetting lens 110 and/or other elements of the eye-implantable device 100. Thus, the eye-implantable device 100 can be operated such that light received from the environment may arrive in focus at the retina, e.g., by operating the electrowetting lens 110 to provide a specified optical power.

The eye-implantable device 100 has been inserted into the eye 10 through an incision 24 formed in the cornea 20 of the eye 10 and then positioned within the lens capsule 40. In order to position the device 100 within the lens capsule 40, a hole 25 has been formed in the lens capsule 40 (e.g., via continuous curvilinear capsulorhexis) and the crystalline lens has been removed (e.g., via ultrasonic phacoemulsification). An eye-implantable device as described herein may be positioned in alternative locations within the eye 10, e.g., within the posterior chamber 11, anterior chamber 12, or in the vitreous humor 13 of the eye 10.

It is noted that relative dimensions in FIG. 1C are not necessarily to scale, but have been rendered for purposes of explanation only in describing the arrangement of the example eye-implantable device 100 within the eye 10. Further, such an implanted device could include multiple elements, located, e.g., in multiple different locations. Such multiple elements could be connected via a cable or by some other means. For example, such an implanted device could include a power reception element and controller that is disposed in the posterior capsule 11 and that is operable to receive wireless power from an eye-mountable device or other external system (not shown) and an electrowetting lens that is disposed within the lens capsule 40 could be operated, by the controller, via a tether connecting the controller and the electrowetting lens, using power from the power reception element.

The eye-implantable device 100 may be rollable, foldable, or otherwise flexible to permit its being rolled, folded, or otherwise manipulated into a smaller shape. This could permit the device 100 to be inserted through a smaller incision through the cornea 20. For example, the device 100 could be rolled up, folded in half, folded in thirds, or manipulated in some other way to permit the device 100 to be inserted through an incision 24 that is less than four millimeters long. In some examples, the device 100 may be rollable, foldable, or otherwise manipulable such that it can be inserted through an incision 24 that is less than 2 millimeters long. In such examples, the eye-implantable device 100 may be unrolled, unfolded, or otherwise manipulated into an operation shape or state (e.g., a substantially flat state) after it is inserted through the incision 24 in the cornea 20 and/or after it has been inserted through some other formed hole or incision (e.g., the hole 25 in the lens capsule) or through some other opening or feature of the eye (e.g., the pupil 26 of the eye 10) to position the device 100 in a specified location of the eye 10.

Note that, while the electrowetting lens 110 is illustrated as containing two fluids 130a, 130b, an electrowetting lens as described herein could be manufactured and distributed containing only one fluid (e.g., an aqueous conductive solution). A second fluid (e.g., an oil or other nonpolar fluid) could later be added to the electrowetting lens. Alternatively, an electrowetting lens as described herein could be manufactured and distributed containing no fluid; subsequently, first and second fluids (e.g., a saline or other polar fluid and an oil or other nonpolar fluid) could be added to the electrowetting lens. Such an electrowetting lens containing only a single fluid or no fluid could be provided to simplify implantation or fabrication of the electrowetting lens. For example, by folding such an electrowetting lens, inserting it into position in an eye, and unfolding the lens before addition of the second fluid and/or first fluid, fouling and/or wetting of internal surfaces of the electrowetting lens by the second fluid (e.g., due to the second fluid contacting the internal surfaces as a result of folding, bending, or otherwise manipulating the electrowetting lens during implantation) and/or dispersion of the first and second fluids into each other can be avoided. The second and/or first fluids can then be added after the electrowetting lens has been unfolded (e.g., via injection through a septum of the electrowetting lens using a needle, via a tubule connected to the electrowetting lens).

Omitting one or more fluids from an electrowetting lens could permit the electrowetting lens to have a smaller volume or thickness and/or could permit the electrowetting lens to be folded and/or rolled into a smaller cross-sectional size or area. Such reductions in the volume, cross-sectional area, or size of the electrowetting lens could permit insertion of the electrowetting lens through smaller incisions than if the electrowetting lens contained the omitted one or more fluids.

An electrowetting lens (e.g., 110) as described herein may be configured in a variety of ways such that a shape of two or more immiscible fluids (e.g., a polar fluid and a nonpolar fluid) can be controlled by the application of a voltage, current, or other electrical signal to electrodes of the electrowetting lens. In some examples, this could include applying, via the electrodes, an electrical field that changes the effective surface energy, surface tension, interfacial energy, or other surface properties of one or more surfaces that at least partially enclose and/or form a lens chamber of the electrowetting lens such that a first one of the immiscible fluids retreats or advances across the one or more surfaces. As the first fluid retreats or advances across the one or more surfaces, the overall shape of the first fluid, and of a contact surface between the first fluid and a second fluid that is immiscible with the first fluid, may change. If the first fluid and second fluid have differing refractive indices, light may be refracted when passing through the electrowetting lens and an amount of that refraction (and a corresponding optical power of the electrowetting lens) could be related to the shape of the contact surface. Thus, the overall optical power of the electrowetting lens can be electronically controlled by applying electrical signals to the electrodes of the electrowetting lens to, e.g., control the shape of one or more fluids within the electrowetting lens and/or to control a shape of a contact surface between such fluids of the electrowetting lens.

FIG. 2A illustrates a cross-sectional view of an example electrowetting lens 200 during a first period of time. The electrowetting lens 200 includes a lens chamber 201 formed from first 210a and second 210b elements. In the example electrowetting lens 200, the lens chamber 201 is radially symmetric about a center line 202. A first electrode 220a is formed along a first internal surface 240a of the first element 210a and takes the form of an inclined ring. A second electrode 220b is formed along a second internal surface 240b of the second element 210b. A first fluid 230a is disposed within the lens chamber 201 and, during the first period of time illustrated in FIG. 2A, is in contact with the first internal surface 240a, the first electrode 220a, a third internal surface 242a, and a fourth internal surface 244a. A second fluid 230b is also disposed within the lens chamber 201 and is, during the first period of time, in contact with the second internal surface 240b and the second electrode 220b. During the first period of time, a contact surface between the first fluid 230a and the second fluid 230b has a first shape 235a. The first 230a and second 230b fluids are immiscible (e.g., the first fluid 230a is a nonpolar fluid and the second fluid 230b is a polar fluid) and have differing refractive indices.

The electrowetting lens 200, as illustrated in FIGS. 2A and 2B, includes two immiscible fluids (230a, 230b). In some examples, the electrowetting lens 200 could be inserted into an eye (e.g., 10) while containing both fluids 230a, 230b. However, in some examples, folding, rolling, or otherwise manipulating the electrowetting lens 200 may cause the fluids to disperse into each other, one of the fluids to contact and/or wet a surface that is normally in contact with another of the fluids, or some other unwanted interaction between the fluids and/or surfaces or materials forming the lens chamber 201. Such unwanted interactions may result in fouling of surfaces that at least partially enclose and/or form the lens chamber 201 with one or both of the fluids 230a, 230b, the formation of droplets or foams within the fluids 230a, 230b, a change in the mechanical, chemical or, electrical properties of one or more surfaces that at least partially enclose and/or form the lens chamber 201 (e.g., a change in the impedance of an electrode surface), a change in the optical properties of the electrowetting lens 200 (e.g., a blurring of image light passed through the lens 200 due to fouling of one or more surfaces that at least partially enclose and/or form the lens chamber 201), or some other deleterious effects.

To prevent such effects, the electrowetting lens 200 could be inserted into an eye and/or undergo additional manipulations while including only one fluid (e.g., while only including the second fluid 230b). That is, the electrowetting lens 200 could be manufactured to include only one fluid and/or a single fluid could be introduced into the electrowetting lens 200 prior to insertion into the eye. A further fluid (e.g., the first fluid 230a) could subsequently be introduced into the lens chamber 201 of the electrowetting lens 200. The further fluid could be introduced after the electrowetting lens 200 has been unrolled, flattened, manipulated to assume a specified shape, manipulated to occupy a specified location within the eye (e.g., a location within the lens capsule of the eye), and/or after some other interaction with the electrowetting lens 200 has occurred.

Additionally or alternatively, one or more manipulations of the electrowetting lens 200 (e.g., manipulating the lens 200 to occupy a specified position within a lens capsule of an eye) could occur after the introduction of the further fluid into the electrowetting lens 200. Manipulations performed subsequent to the introduction of the further fluid into the electrowetting lens 200 could be selected due to difficulty in performing the selected manipulations before introduction of the further fluid, due to the presence or tubes or other means used to introduce the further fluid into the electrowetting lens 200, due to a relatively low probability of occurrence of surface fouling, fluid dispersion, or other deleterious effects or processes due to performance of the selected manipulations, or due to some other considerations.

A second (or further) fluid could be introduced into the lens chamber 201 via one or more of a variety of methods. In some examples, the electrowetting lens 200 and/or components thereof could be penetrated by a needle and the further fluid (e.g., 230a) could be introduced into the lens chamber 201 via the needle. Additionally or alternatively, the further fluid could be introduced via a tube or duct that is formed from or otherwise attached to the electrowetting lens 200. Other methods may also be used to introduce one or more fluids into the electrowetting lens 200.

The electrowetting lens could include one or more features or elements to facilitate penetration of the electrowetting lens 200 and/or introduction of a fluid into the electrowetting lens 200 via such penetration. In the example shown in FIGS. 2A and 2B, the electrowetting lens 200 includes a septum 250 that can be penetrated by a needle (or other implement) to permit introduction of one or more fluids into the lens chamber 201. The septum 250 could be composed of silicone rubber, self-healing materials, and/or other materials to reduce or prevent a flow of fluid into and/or out of the lens chamber 201 following removal of a needle used to penetrate the septum 250. Additionally or alternatively, fluids to be removed from the lens chamber 201 using the septum 250. For example, an amount of the second fluid 230b could be removed from the lens chamber 201 before and/or after introduction of the first fluid 230a into the lens chamber 201 (e.g., to control a total volume of the fluids 230a, 230b within the lens chamber 201, to control a pressure within the lens chamber 201, to control a volume or geometry of the lens chamber 201).

The septum 250 is disposed within a fluid pathway 255 into the lens chamber 201 from outside of the electrowetting lens 200. When a needle, tube, or other penetrating means is not penetrating the septum 250, the septum 250 blocks the flow of fluid from outside of the electrowetting lens 200 (e.g., from an aqueous humor of an eye) into the lens chamber 201 via the fluid pathway 255. Such a fluid pathway could include one or more channels, tubes, microfluidic features, or other formed elements disposed between the lens chamber 201 and the external environment of the electrowetting lens 200. For example, a septum could be disposed at a first location of the electrowetting lens and/or an eye-implantable device that includes the electrowetting lens. The first location could be located away from a center of the electrowetting lens, e.g., to reduce an effect of the septum on the optical properties of the electrowetting lens or to simplify penetration of the septum by a needle. Such a fluid pathway could further include one or more channels between the lens chamber and the septum. Such channel(s) could be provided to control a location at which fluid(s) are introduced into the lens chamber and/or removed from the lens chamber, e.g., to prevent contact between an introduced fluid and one or more surfaces that at least partially enclose and/or form the lens chamber, to facilitate rinsing of the lens chamber by one or more fluids (e.g., to remove bubbles from the lens chamber), to facilitate the suction from the lens chamber of a particular one of one or more fluids and/or volumes of fluids present within the lens, or to provide some other benefit.

Fluid(s) could be introduced into the lens chamber 201 and/or removed from the lens chamber 201 by some additional or alternative means or methods. In some examples, one or more tubes (not shown) could protrude from the electrowetting lens 200 and/or an eye-implantable device that includes such a lens. Such a tube could provide at least a portion of a fluid pathway into the lens chamber 201 from outside of the electrowetting lens 200. Such a tube could provide a means for introducing one or more fluids (e.g., the first fluid 230*a*) into the lens chamber 201, e.g., from outside of an eye into which the electrowetting lens 200 has been inserted. For example, the electrowetting lens could be inserted through an incision into an eye and manipulated (e.g., to unroll or unfold the electrowetting lens from a rolled or folded state) in such a way that a tube extends from the electrowetting lens 200 to the outside of the eye (e.g., through the incision in the cornea of the eye through which the electrowetting lens 200 was inserted). One or more fluids could then be introduced into the lens chamber 201 and/or removed from the lens chamber via the tube.

Such a tube could be configured to facilitate closure of portions of the tube, e.g., to inhibit fluid flow into and/or out of the lens chamber 201 after the one or more fluids have been introduced into the electrowetting lens 200 and/or removed from the electrowetting lens 200 via the tube. For example, the tube could include a crimpable portion that could be crimped to inhibit fluid flow out of and/or into the lens chamber 201 or other portions of the electrowetting lens 200. Crimping such a crimpable portion of the tube could include applying mechanical pressure to deform or otherwise modify the crimpable portion of the tube to close the crimpable portion. Additionally or alternatively, acoustical (e.g., ultrasound), light, thermal, and/or other energy sources could be applied to crimp the crimpable portion, e.g., by causing the material of the crimpable portion to melt, undergo a chemical change, or some other process that results in inhibition of fluid flow through the crimped portion of the tube.

The crimpable portion of the tube could be similar to other portions of the tube (e.g., the tube could be a single piece of a single material) or could differ in one or more respects to the remainder of the tube. For example, the crimpable portion could have a material composition that differs from other portions of the tube, e.g., to facilitate melting of the material of the crimpable portion. In another example, the crimpable portion could include an interior coating or other material configured to act as a contact adhesive, to act as a photo-curable polymer or adhesive, or to otherwise facilitate sealing of the crimpable portion after crimping.

After introducing fluid(s) into the lens chamber 201 and/or performing some other fluid transfer(s) via the tube, the tube could be cut or otherwise sectioned and the cut portion of the tube (that is, the portion disconnected from the electrowetting lens 200 and/or an eye-implantable device that includes the electrowetting lens 200 following sectioning of the tube) could be removed from the eye. This could include applying mechanical forces (e.g., using a scalpel, scissors, or other bladed implements), ultrasonic energy, light energy (e.g., a laser), or some other energies or forces to cut the tube. In some examples, crimping the tube and cutting the tube could be performed at the same time, e.g., by application of ultrasonic energy to seal the tube together and to section the tube. The tube could include features to facilitate cutting and/or sectioning the tube at one or more specified locations. For example, the tube could include a material configured to preferentially absorb light or acoustical energy at a particular frequency. In another example, the tube could be scored or include other formed features that facilitate sectioning of the tube, e.g., by application of shear forces or tensions to the tube.

Such a tube could be in direct fluid communication with the lens chamber 201 (e.g., the tube could be disposed such that it connected directly to/through a wall of the lens chamber 201). Additionally or alternatively, such a tube could be in fluid communication with the lens chamber 201 or with some other volume or elements of the electrowetting lens 200 (e.g., a fluid reservoir, an element of a microfluidic actuator) via one or more channels. For example, a tube could connect to an electrowetting lens at a first location of the electrowetting lens and/or of an eye-implantable device that includes the electrowetting lens. The first location could be located away from a center of the electrowetting lens, e.g., to reduce an effect of the tube (e.g., of a segment of the tube that remains connected to the lens after crimping and/or cutting the tube) on the optical properties of the electrowetting lens or to simplify crimping, cutting, or other interactions or manipulations of the tube. The tube could be in fluid communication with the lens chamber (or other elements) of the electrowetting lens via a fluid pathway that includes one or more channels between the lens chamber and the tube. Such channel(s) could be provided to control a location at which fluid(s) are introduced into the lens chamber and/or removed from the lens chamber, e.g., to prevent contact between an introduced fluid and one or more surfaces that at least partially enclose and/or form the lens chamber, to facilitate rinsing of the lens chamber by one or more fluids (e.g., to remove bubbles from the lens chamber), to facilitate the suction from the lens chamber of a particular one of one or more fluids and/or volumes of fluids present within the lens, or to provide some other benefit.

The electrowetting lens 200 could include further elements or features to facilitate the addition, removal, or other interaction with one or more fluids of the electrowetting lens 200 and/or to provide some other benefit(s). For example, the electrowetting lens 200 could include channels, valves, fluidic pathways, microfluidic elements, or other elements or features configured to provide means for fluid to leave the lens chamber 201 or other volumes of the electrowetting lens 200. Such means could be provided to allow fluid (e.g., the second fluid 230*b*) to exit the lens chamber 201 into the environment of the electrowetting lens 200 (e.g., into a lens capsule of an eye). Such fluid could exit the lens chamber 201 as a result of the introduction of fluid into the lens chamber 201, e.g., via the septum 250, a tube, or some other means.

The introduced fluid could be a fluid not previously present in the lens chamber 201 (e.g., an oil or other component of the first fluid 230*a* that was omitted from the electrowetting lens 200 prior to implantation to prevent fouling of surfaces that at least partially enclose and/or form the lens chamber 201 during implantation of the electrowetting lens 201 or to provide some other benefit). Additionally or alternatively, an introduced fluid could be of the same type as a fluid already present in the electrowetting lens 201, e.g., to rinse out the lens chamber 201, to remove gases (e.g., gases dissolved in the second fluid 230*b* that could form bubbles within the lens chamber 201) from the lens chamber 201, to control a volume or internal pressure of the lens chamber 201, or to provide some other benefit.

The electrowetting lens 200 could include one or more channels or other elements that are in fluid communication with the lens chamber 201 and with the environment of the electrowetting lens 200 (e.g., with aqueous humor within a lens capsule of an eye) and that provide a means for fluid flow into and/or out of the lens chamber 201 (e.g., as a result of the addition of fluids to the lens chamber 201 via the septum 250) and/or between volumes of the electrowetting lens. Such channels could allow unimpeded fluid flow between the lens chamber 201 and the environment of the electrowetting lens 201, e.g., to permit excess fluid to exit the lens chamber as the first fluid 230a is introduced via the septum 250, to permit the movement of solutes or other substances between the second fluid 230b and the aqueous humor of an eye, or to provide some other benefit. Additionally or alternatively, such channels could include means to impede fluid flow into and/or out of the lens chamber 201.

For example, the electrowetting lens 200 may include a valve 260 that blocks a fluid pathway 265 provided by a channel formed in the electrowetting lens 200. The valve 260 impedes fluid flows into the lens chamber 201 more than fluid flows out of the lens chamber 201, such that an amount of the second fluid 230b may flow out of the lens chamber 201 into an environment of the electrowetting lens 200 (e.g., into a lens chamber of an eye) as a result of the introduction of the first fluid 230a to the lens chamber 201 (e.g., via the septum 250, via a tube). Such a fluid pathway could include other means to impede or block fluid flows into and/or out of the lens chamber 201, e.g., by including a septum that may be pierced by a needle to permit fluid flows, by including a tube that protrudes from the electrowetting lens 200 and that may be crimped and/or cut, by including a filter, or by being configured in some other way.

The electrowetting lens 200 could include additional or alternatively elements or features for facilitating and/or controlling the flow of fluid into and/or out of the lens chamber 201 (e.g., out of and/or into an environment surrounding the electrowetting lens 200) and/or between some other volume(s) of the electrowetting lens 200 (e.g., between one or more reservoirs, electrowetting actuators, or microfluidic channels and the lens chamber 201). The electrowetting lens could include multiple septa, multiple channels, multiple valves, multiple tubes, or multiple of other features or elements. These additional or alternative features could facilitate introduction of one or more fluids via multiple fluid pathways (e.g., to facilitate even filling of the lens chamber 201 with the first fluid 230a such that the first fluid 230a does not wet the second internal surface 240b), could facilitate extraction or removal of fluid(s) via multiple fluid pathways, could facilitate removal of fluid(s) via one or more fluid pathways while fluid is introduced via one or more other fluid pathways (e.g., to facilitate rinsing of the lens chamber 201 by an amount of the second fluid 230b, to facilitate removal of an amount of the second fluid 230a while an amount of the first fluid 230a is introduced into the lens chamber 201), or could provide some other benefit. For example, the electrowetting lens 200 could include one or more septa in addition to the illustrated septum 250; such septa could be penetrated by respective different needles (e.g., by needles that are mechanically coupled together to facilitate alignment with the respective septa). In other examples, the electrowetting lens 200 could include multiple tubes (not shown); such tubes could be coupled and/or formed together, e.g., to facilitate crimping or cutting of the multiple tubes.

As the first 230a and second 230b fluids differ with respect to refractive index, light that passes through the contact surface (e.g., light that is passing through the electrowetting lens 200 along the center line 202) may be refracted. A degree or amount of the refraction, and a related optical power of the electrowetting lens 200, may be related to the shape of the contact surface between the first fluid 230a and the second fluid 230b.

The refractive indices of the two fluids 230a, 230b may differ by a specified amount. The optical power of the electrowetting lens 200 (e.g., the controllable range of optical powers of the electrowetting lens 200) may be related to the magnitude of the difference between the refractive indices. The refractive indices of the two fluids 230a, 230b could differ by more than 0.1. The difference between the refractive indices could be controlled by controlling and/or modifying the refractive index of one or both of the fluids 230a, 230b.

The refractive index of an aqueous fluid (e.g., the second fluid 230b) may be approximately equal to 1.33, the refractive index of water. Alternatively, butanediol or some other substance(s) could be added to such an aqueous solution such that the refractive index of the aqueous solution differs from 1.33. In examples where a substance is added to an aqueous (or other) fluid of the electrowetting lens 200, the electrowetting lens 200 may include a seal or coating to seal the lens chamber (e.g., to hermetically seal the lens chamber) to prevent such a substance from exiting the electrowetting lens 200 and entering the aqueous humor of an eye.

Properties of a nonpolar fluid (e.g., the first fluid 230a) could additionally or alternatively be specified to control the refractive index of the nonpolar fluid. This could include adding substances to the nonpolar fluid. For example, a phenylated silicone oil (e.g., polyphenylmethylsiloxane) could be added to a silicone oil (e.g., to polydimethylsiloxane) to increase its refractive index. Additionally or alternatively, a ratio of components of a nonpolar fluid could be specified to control the refractive index of the nonpolar fluid. For example, a ratio between a first linear alkane (e.g., hexadecane) and a second linear alkane (e.g., nonadecane) could be specified to control the refractive index of the nonpolar fluid. Yet further, a polymer length, a polydispersity, a degree of branching, or some other properties of a nonpolar fluid could be specified to control the refractive index of the nonpolar fluid and/or to control some other property (e.g., melting point, viscosity, surface energy, density) of the nonpolar fluid.

The shape of the contact surface can be controlled by applying an electrical signal to the electrodes 220a, 220b, e.g., by applying an electrical voltage to the electrodes 220a, 220b. The voltage applied to the electrodes 220a, 220b may be related to the steady-state (e.g., following any transient changes in the electrowetting lens resulting from changes in the applied voltage) optical power of the electrowetting lens 200 and/or the shape of the contact surface between the fluids 230a, 230b. The specific relationship could be based on an effect on the surface energy of the first internal surface 240a relative to each of the fluids 230a, 230b, to an effective capacitance between the first electrode 220a and the second electrode 220a via a conductive second fluid 230b (e.g., via a second fluid 230b that includes a conductive, aqueous solution and that is in conductive and/or capacitive electrical contact with the second electrode 220b), or to some other factors.

The first electrode 220a and second electrode 220b could include conductive materials (e.g., aluminum, gold, copper, or other materials) disposed on respective internal surfaces of the first element 210a and second element 210b. Such deposition could include forming the electrodes in place (e.g., by sputtering, chemical vapor deposition, polymerization, deposition of a carrier fluid containing nanowires or other materials in suspension followed by evaporation of the carrier fluid, by photolithography or other processes for patterning or etching materials in place) and/or forming the electrodes and subsequently disposing them on internal surfaces of the elements 210a, 210b (e.g., by using an adhesive to adhere a metal foil, wire, rod, cone, textured surface, or other formed conductive material to a surface of one or both of the elements 210a, 210b). Additionally or alternatively, one or both of the electrodes 220a, 220b could include wires, rods, cones, textured surfaces, or other elements that are disposed on and/or that penetrate through an internal surface of one or both of the elements 210a, 210b and that protrude into the lens chamber 201.

One or both of the electrodes could further include a dielectric layer disposed between such a conductive material and the inside of the lens chamber 201. For example, the first electrode 220a could include such a dielectric layer. Such a dielectric layer could be provided to prevent large, direct currents from passing from the first electrode 220a into one or both of the first 230a or second 230b fluids, to provide a capacitive electrical coupling between the first electrode 220a and such fluids, to limit an amount of charge that can be transmitting into such fluids via the first electrode 220a, or to provide some other benefits.

Such a dielectric layer could be a separate material (e.g., parylene) deposited on the conductive material (e.g., via CVD, spin coating, or some other process). Additionally or alternatively, the dielectric layer of the first electrode 220a could be formed from the conductive material of the electrode, e.g., the dielectric layer could be a nonconductive layer of aluminum oxide formed by oxidation of an underlying aluminum metal of the first electrode 220a. Such a dielectric layer could be formed via anodization or other electrically-driven reactions at the surface of the electrode. Additionally or alternatively, such a dielectric layer could be formed by redox reactions between the fluids in the lens chamber 201 and the material of the electrode.

In some examples, the formation and/or maintenance of such a dielectric layer could be negatively impacted by the presence of certain ions within the lens chamber 201 (e.g., dissolved in one or both of the fluids 230a, 230b). For example, the presence of chloride ions could act to pit or otherwise damage a dielectric layer of aluminum oxide that has formed on the surface of an aluminum electrode. In such examples, a barrier could be formed from a chloride-impermeable material to prevent chloride ions present in the aqueous humor (or in some other environment to which the lens 200 is exposed) from entering the lens chamber 201 or from entering some other material or volume of the lens 200. Such a material could include a polymeric material, a metal foil or deposited metal layer, or some other material(s). Such materials could be substantially transparent to visible light.

The voltage between the electrodes 220a, 220b could be controlled in order to control the optical power of the electrowetting lens 200 by controlling the shape of the contact surface between the fluids 230a, 230b. FIG. 2B illustrates the electrowetting lens 200 during a second period of time during which a voltage is being applied to the electrodes 220a, 220b such that the contact surface between the first fluid 230a and the second fluid 230b has a second shape 235b. As a result, the optical power of the electrowetting lens 200 during the second period of time is different than the optical power of the electrowetting lens 200 during the first period of time.

The particular shape of the contact surface and/or of the geometry of the fluids 230a, 230b could be related to the applied voltage and to a variety of other factors. Such factors could include the interfacial energy between the fluids 230a, 230b, the interfacial energy between the fluids 230a, 230b and the internal surfaces 240a, 242a, 244a, 240b, the geometry of the internal surfaces 240a, 242a, 244a, 240b, a geometry of the electrodes 220a, 220b, and/or a geometry of a dielectric layer of the first electrode 220a. One or more of these factors could be specified in order to affect the shape of the contact surface between the fluids 230a, 230b, to affect the geometry and/or location of the fluids 230a, 230b within the lens chamber 201, to affect the relationship between an applied voltage and the optical power of the electrowetting lens 200, or to affect some other property of interest of the electrowetting lens 200.

This could include adding surfactants, polar and/or ionic substances, nonpolar substances, to the fluid(s) or otherwise specifying a composition of the first 230a and/or second 230b fluids to control an interfacial energy between the fluids 230a, 230b and/or to control an interfacial energy between the fluids and the internal surfaces 240a, 242a, 244a, 240b. Additionally or alternatively, the composition of the material composing the internal surfaces 240a, 242a, 244a, 240b could be specified to control the interfacial energy between the internal surfaces and the fluids.

This could include selecting the bulk materials of the first 210a and second 210b elements and/or providing one or more coatings or surface treatments to the internal surfaces of the first 210a and/or second 210b elements. For example, the first fluid 230a could be an oil or other nonpolar fluid and one or more of the first 240a, third 242a, or fourth 244a internal surfaces could be superhydrophobic or otherwise hydrophobic. Further, the second fluid 230b could be a polar fluid (e.g., could include a saline solution or other aqueous solution) and the second 240b internal surface could be superhydrophilic or otherwise hydrophilic (e.g., by including a surface coating, by including a surface features or textures, by having been exposed to an oxidization process, or by some other means).

The distribution of such coatings or materials on the internal surfaces of the first 210a and/or second 210b elements and/or the geometry of such surfaces could be specified to center the first fluid 230a along the center line 202 or along some other specified axis of the electrowetting lens 200. This could include applying different coating or other material to internal surfaces according to distance from the center line 202. Additionally or alternatively, a thickness or other property of a dielectric of the first electrode 220a could vary according to distance from the center line 202 such that, when a voltage is applied between the electrodes 220a, 220b, electrical and/or interfacial forces applied to the first 230a and/or second 230b fluids tend to center the first fluid 230a along the center line 202 and/or to conform a boundary between the fluids 230a, 230b on the first internal surface 240a to a circle centered on the center line 202.

The lens chamber 201 could be permeable to water or other substances (e.g., ions) in aqueous humor of an eye. This could include the first 210a and/or second 210b elements being composed at least partially of a polymeric material that is permeable to water (or other substances) in the aqueous humor. In examples wherein the lens chamber is permeable to a substance that is present in the aqueous humor, one or both of the fluids 230a, 230b could include a concentration of the substance corresponding to the concentration of the substance in the aqueous humor, e.g., to prevent a net flow of the substance from the aqueous humor into the fluids 230a, 230b or vice versa.

Additionally or alternatively, the lens chamber could be made impermeable to such substances in the aqueous humor and/or to substances in one or both of the fluids 230a, 230b. For example, one of the fluids could be a conductive fluid that includes butanediol, and the lens chamber could be made impermeable to butanediol and/or could be hermetically sealed. This could include constructing the lens chamber from materials that are impermeable to the substances. Additionally or alternatively, a barrier layer or coating could be formed from such impermeable materials to prevent the substances from entering the lens chamber 201 or some other element or structure of the electrowetting lens 200. For example, a barrier could be formed (e.g., on an internal surface of the first 210a and/or second 210b elements) from a chloride-impermeable material to prevent chloride ions present in the aqueous humor from entering the lens chamber 201 or from entering some other material or volume of the lens 200. Such a material could include a polymeric material, a metal foil or deposited metal layer, or some other material(s). Such materials could be substantially transparent to visible light.

In some examples, components of the electrowetting lens 200 could be composed of a self-healing material. For example, the first 210a and/or second 210b elements could be at least partially formed from self-healing materials. Additionally or alternatively, one or more septa (e.g., 250) of the electrowetting lens 200 could be at least partially formed from self-healing materials. Such self-healing materials could be provided to maintain the integrity of the lens chamber 201 or of other volumes of the electrowetting lens 200 against bulk fluid flows into or out of such volumes (e.g., between the lens chamber 201 and the aqueous humor of an eye). In some examples, such self-healing materials may be degraded and/or their ability to self-heal diminished by exposure to chloride ions or other substances present in the aqueous humor and/or in the fluids 230a, 230b of the electrowetting lens 200. In such examples, an impermeable material (e.g., a chloride-impermeable material) could be used to form a barrier between the chloride ions or other substances present in the aqueous humor and the self-healing material.

III. EXAMPLE FILLING OF AN ELECTROWETTING LENS

It can be beneficial for one or more substances of an electrowetting lens (e.g., an oil, a saline solution, or some other fluid of the lens) to be omitted from the electrowetting lens during implantation of the electrowetting lens into an eye. The omitted substance or substances can then be introduced into the electrowetting lens (e.g., via a needle, via a tube, via some other means) following the implantation. Omitting such substance(s) from the lens can prevent dispersion of the substances into each other and/or wetting of internal surfaces by the omitted substances during folding, rolling, unfolding, unrolling, or other manipulations of the electrowetting lens (e.g., of a flexible electrowetting lens) during implantation or during other processes (e.g., during fabrication of the electrowetting lens). By preventing dispersion of the substances into each other and/or preventing wetting of internal surfaces by one or more substances, optical properties (e.g., clarity, symmetry of refraction about an axis, wavelength-dependent refraction or absorption) or other properties (e.g., of the relationship between an applied voltage and the optical power of the lens) of the electrowetting lens may be preserved and/or improved. Further, omission of one or more fluids from the electrowetting lens during implantation could reduce the volume, thickness, cross-section area when folded or rolled, or other dimensions of the electrowetting lens, permitting the electrowetting lens to be inserted through a smaller incision.

For electrowetting lenses that include two immiscible fluids (e.g., an oil and a saline solution, or some other set of a nonpolar fluid and a polar fluid), this can include fabricating the electrowetting lens to include only one of the immiscible fluids (e.g., to include only the saline solution). Such a single-fluid electrowetting lens can then be inserted into an eye, rolled, folded, unrolled, unfolded, or otherwise manipulated into order to dispose the electrowetting lens within an eye (e.g., within a lens capsule of the eye). Following the insertion or other manipulations, the other of the two immiscible fluids (e.g., the oil) can be introduced into the electrowetting lens to facilitate operation of the electrowetting lens to electronically control the optical power of the electrowetting lens. Alternatively, a fluid present in the electrowetting during implantation could be completely replaced within the electrowetting lens by two (or more) immiscible fluids following implantation. For example, a first saline solution present within a lens chamber of an electrowetting lens could be replaced with a second saline solution (e.g., a second saline solution that has had dissolved gases removed from it to prevent the development of gas bubbles within the lens chamber) and/or rinsed with a further amount of the first saline solution (e.g., to remove bubbles or other substances from the lens chamber). Subsequently, an oil could be introduced into the lens chamber. In further examples, neither fluid could be present in the electrowetting lens, and both fluids (e.g., a saline and an oil) could be introduced into the electrowetting lens subsequent to inserting the electrowetting lens into an eye.

One or more fluids could be introduced into and/or removed from an electrowetting lens via a variety of different means. The electrowetting lens could include tubes, septa, channels, valves, reservoirs or other chambers, or other features or elements to facilitate such introduction and/or removal of fluid from the electrowetting lens.

Figure 3A:
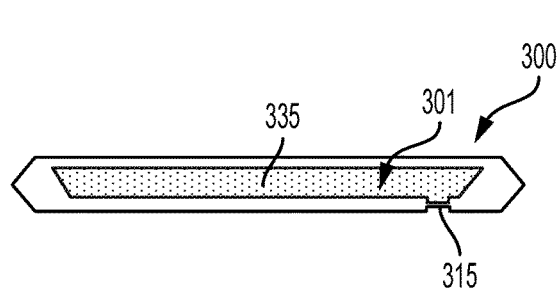
FIG. 3A is a side cross-section view of an example eye-implantable device.

FIG. 3A shows an example electrowetting lens 300 (e.g., of an eye-implantable device) that includes a first fluid 335 (e.g., a saline solution) disposed within a lens chamber 301 of the electrowetting lens 300. The electrowetting lens 300 includes a septum 315 that blocks a fluid pathway into the lens chamber 301 from outside of the electrowetting lens 300.

The electrowetting lens 300 could be fabricated in a variety of ways. In some examples, the lens chamber 301 could be partially formed (e.g., by injection molding or otherwise forming a polymeric material that at least partially forms the lens chamber 301) and the first fluid deposited within the lens chamber 301. The lens chamber 301 could then be completed, e.g., by disposing and/or forming a lid atop the portions of the chamber already formed. In some examples, this could include filling the partially-formed lens chamber with a first fluid 330 comprising saline (or some other aqueous solution) and displacing any bubbles formed on the walls of the lens chamber (e.g., by ultrasonic cleaning, by rinsing, by adding the saline in a reduced-pressure environment, and/or by degassing the saline prior to applying it to the lens chamber).

Figure 3B:
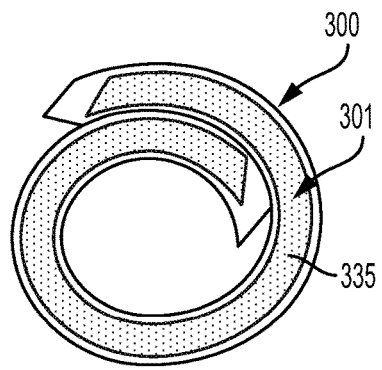
FIG. 3B is a side cross-section view of the example eye-implantable device of FIG. 3A after being rolled up.

Once the electrowetting lens 300 has been fabricated, the electrowetting lens may be folded, rolled, bent, or otherwise manipulated. Such manipulation could permit the electrowetting lens to be inserted via an incision that is smaller than a diameter or other characteristic dimension of the electrowetting lens. For example, the electrowetting lens could be rolled, folded, or otherwise manipulated such that it can be inserted through an incision that is less than 4 millimeters wide, or less than 2 millimeters wide. FIG. 3B shows the electrowetting lens 300 rolled up. Note that an electrowetting lens could be rolled more or fewer times, or could be rolled more tightly or more loosely, or could differ in some other respect from that shown in FIG. 3B. Additionally or alternatively, the electrowetting lens 300 could be folded one or more times to facilitate insertion into an eye through an incision.

Figure 3C:
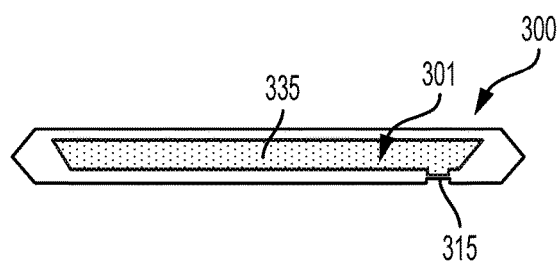
FIG. 3C is a side cross-section view of the example eye-implantable device of FIG. 3B after being unrolled.

Once inserted into an eye (e.g., via an incision), the electrowetting lens may be positioned, flattened, or otherwise manipulated to facilitate operation of the electrowetting lens to provide an electronically-controllable optical power to an eye. This is shown in FIG. 3C, which shows the electrowetting lens 300 unrolled. A second fluid (e.g., an oil or other nonpolar fluid) that is immiscible with the first fluid 335 may then be introduced into the lens chamber 301. This could be accomplished by piercing the septum 315 (e.g., with a needle) and introducing the second fluid via the puncture.

Figure 3D:
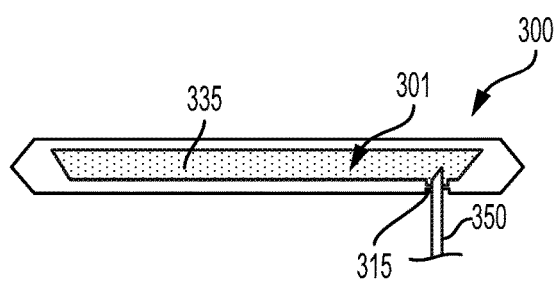
FIG. 3D is a side cross-section view of the example eye-implantable device of FIG. 3C after being penetrated by a needle.

FIG. 3D shows a needle 350 piercing the septum 315 to provide access to the inside of the lens chamber 301. The needle 350 could be part of a syringe, a laparoscopic implement, or part of some other system or device. The needle 350 may include one or more tubes, chambers, pipes, or other elements that form one or more fluid pathways to facilitate fluid flow into and/or out of the lens chamber 301 via the needle 350. The needle 350 could be connected (e.g., via tubes, pipes, channels, or other elements or formed features) to a reservoir, a pump, or other elements that are configured to provide a fluid (e.g., to provide an oil, to provide a saline solution), to receive a fluid, to apply a pressure, or to provide some other force or substance. Such a source of fluid (e.g., a source of saline) could include means for removing dissolved gases from the fluid (e.g., to prevent the development of bubbles in the lens chamber 301 following introduction of the fluid). Additionally or alternatively, the fluid could be received in a substantially gas-free state (e.g., the fluid could be provided in a gas-impermeable ampoule or other gas-impermeable package). The electrowetting lens 300 could include fiducials, tabs, or other features to facilitate the needle 350 piercing the septum 315 and/or to facilitate holding or manipulation of the electrowetting lens 300 while the septum 315 is pierced.

Figure 3E:
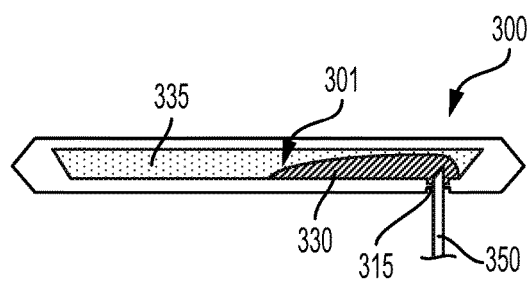
FIG. 3E is a side cross-section view of the example eye-implantable device of FIG. 3D while being filled with a fluid via the needle.

FIG. 3E shows a second fluid 330 (e.g., a silicone oil or other nonpolar fluid) being introduced into the lens chamber 301 via the needle 350 while the needle 350 is penetrating the septum 315. A pressure, a flow rate, or some other property of the introduction of the second fluid 330 could be controlled in order to reduce the risk of the second fluid 330 contacting and/or wetting a particular surface within the electrowetting lens 300, to reduce the risk of the first 335 and second 330 fluids dispersing into each other, to reduce the risk of the lens chamber 301 being damaged, to reduce the risk of bubbles forming in either of the first 335 or second 330 fluids, to allow an amount of the first fluid 335 to exit the lens chamber 301 via a channel, valve, or other means, or to provide some other benefit.

In some examples, the electrowetting lens 300 could include a tube (not shown) that protrudes from the electrowetting lens 300 and/or from an eye-implantable device that includes the electrowetting lens 300. Such a tube could provide at least a portion of a fluid pathway from the lens chamber 301 to outside of the electrowetting lens 300. For example, an amount of the first fluid 335 could flow out of the lens chamber 301 through the tube as a result of the introduction of the second fluid 330. Such a tube could be crimped, following introduction of the second fluid 330 and/or following some other processes, to inhibit fluid flow into or out of the electrowetting lens 300 via the tube.

Figure 3F:
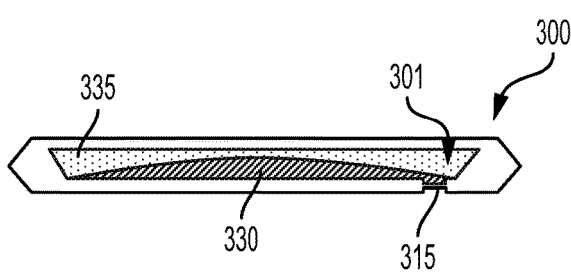
FIG. 3F is a side cross-section view of the example eye-implantable device of FIG. 3E after being filled with the fluid via the needle.

FIG. 3F shows the electrowetting lens 300 after the second fluid 330 has been introduced and after the needle 350 has been retracted from the septum 315. The electrowetting lens 300 could be operated (e.g., by applying a voltage to electrode(s) of the electrowetting lens 300) to electronically provide a controllable optical power.

In order to prevent the second fluid 330 from wetting or fouling specified surfaces within the electrowetting lens 300, to prevent dispersion of the fluids 330, 335, or to provide some other benefits, the second fluid 330 could be introduced into the lens chamber 301 after insertion of the lens into the eye, after positioning the lens at a specified location within the eye, after unfolding or unrolling the lens, or after some other processes have occurred.

Note that the needle 350 could be used to introduce and/or remove other fluids into/from the lens chamber 301. For example, the needle 350 could be used to remove an amount of the first fluid 335 from the lens chamber 301. Additionally or alternatively, the needle 350 could be used to provide an amount of the first fluid 335, or of some other fluid, to rinse the lens chamber 301. Such rinsing could be performed to remove bubbles or other debris (e.g., fragments of electrode material) from the lens chamber 301, to ensure that the first fluid 335 present in the lens chamber 301 following such rinsing contains a specified low amount of dissolved gases, or to provide some other benefit. The needle 350 could include multiple channels or other fluid pathways, e.g., such that the second fluid 330 may be introduced via a first channel and an amount of the first fluid 335 may be removed and/or introduced (e.g., to rinse the lens chamber 301) via a second channel. Additionally or alternatively, multiple needles could be used to introduce and/or remove fluid(s) from the lens chamber 301 via respective multiple septums.

FIG. 4A shows another example electrowetting lens 400 (e.g., of an eye-implantable device) that includes a first fluid 435 (e.g., a saline solution) disposed within a lens chamber 401 of the electrowetting lens 400. The electrowetting lens 400 includes a first tube 425 that protrudes from the electrowetting lens 400 and that provides a portion of a first fluid pathway 415 into the lens chamber 401 from outside of the electrowetting lens 400 (e.g., from outside of an eye-implantable device that includes the electrowetting lens 400). The electrowetting lens 400 also includes a second tube 427 that protrudes from the electrowetting lens 400 and that provides a portion of a second fluid pathway 417 into the lens chamber 401 from outside of the electrowetting lens 400.

The electrowetting lens 400 could be fabricated in a variety of ways. In some examples, the lens chamber 401 could be partially formed (e.g., by injection molding or otherwise forming a polymeric material that at least partially forms the lens chamber 401) and the first fluid 435 deposited within the lens chamber 401. The lens chamber 401 could then be completed, e.g., by disposing and/or forming a lid atop the portions of the chamber already formed. In some examples, this could include filling the partially-formed lens chamber with a first fluid 430 comprising saline (or some other aqueous solution) and displacing any bubbles formed on the walls of the lens chamber (e.g., by ultrasonic cleaning, by rinsing, by adding the saline in a reduced-pressure environment, and/or by degassing the saline prior to applying it to the lens chamber). The first 425 and second 427 tubes could be formed along with other components of the electrowetting lens 400 (e.g., with one or more elements forming the lens chamber 401) via a process of injection molding or some other process. Additionally or alternatively, the tube(s) 425, 427 could be formed separately and then attached to the electrowetting lens 400 (e.g., by using an adhesive, by applying heat to partially melt a material of the tube(s), or by some other method).

Once the electrowetting lens 400 has been fabricated, the electrowetting lens may be folded, rolled, bent, or otherwise manipulated. Such manipulation could permit the electrowetting lens to be inserted via an incision that is smaller than a diameter or other characteristic dimension of the electrowetting lens. For example, the electrowetting lens could be rolled, folded, or otherwise manipulated such that it can be inserted through an incision that is less than 4 millimeters wide, or less than 2 millimeters wide. FIG. 4B shows the electrowetting lens 300 folded into thirds. Note that an electrowetting lens could be folded more or fewer times or could differ in some other respect from the folded electrowetting lens 400 shown in FIG. 4B. Additionally or alternatively, the electrowetting lens 400 could be rolled one or more times to facilitate insertion into an eye through an incision.

Once inserted into an eye (e.g., via an incision), the electrowetting lens may be positioned, flattened, or otherwise manipulated to facilitate operation of the electrowetting lens to provide an electronically-controllable optical power to an eye. This is shown in FIG. 4C, which shows the electrowetting lens 400 flattened. A second fluid (e.g., an oil or other nonpolar fluid) that is immiscible with the first fluid 435 may then be introduced into the lens chamber 401. This could be accomplished by introducing the second fluid via one or both of the tubes 425, 427.

The tubes 425, 427 may extend out of the incision in the eye and be connected to devices or systems configured to provide fluid(s) to the lens chamber 401 and/or to extract or otherwise receive fluid(s) from the lens chamber 401. The tubes 425, 427 could be connected to reservoirs, pumps, or other elements that are configured to provide a fluid (e.g., to provide an oil, to provide a saline solution), to receive a fluid, to apply a pressure, or to provide some other force or substance. Such a source of fluid (e.g., a source of saline) could include means for removing dissolved gases from the fluid (e.g., to prevent the development of bubbles in the lens chamber 401 following introduction of the fluid). Additionally or alternatively, the fluid could be received in a substantially gas-free state (e.g., the fluid could be provided in a gas-impermeable ampoule or other gas-impermeable package).

Figure 4D:
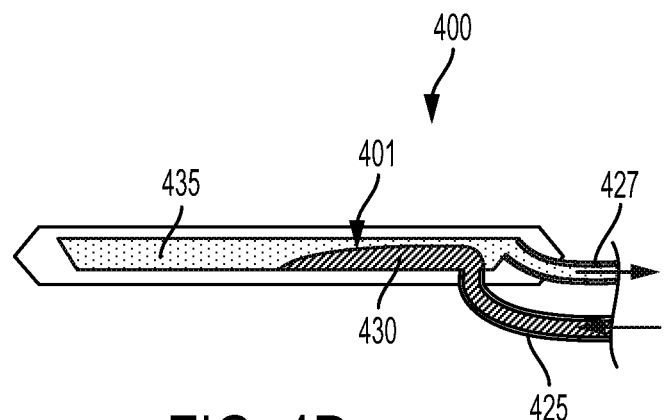
FIG. 4D is a side cross-section view of the example eye-implantable device of FIG. 4C while being filled with a fluid via a tube.

FIG. 4D shows a second fluid 430 (e.g., a silicone oil or other nonpolar fluid) being introduced into the lens chamber 401 via the first tube 425. A pressure, a flow rate, or some other property of the introduction of the second fluid 430 could be controlled in order to reduce the risk of the second fluid 430 contacting and/or wetting a particular surface within the electrowetting lens 400, to reduce the risk of the first 435 and second 430 fluids dispersing into each other, to reduce the risk of the lens chamber 401 being damaged, to reduce the risk of bubbles forming in either of the first 335 or second 430 fluids, to allow an amount of the first fluid 435 to exit the lens chamber 401 via a channel, valve, or other means, or to provide some other benefit. FIG. 4D also shows an amount of the first fluid 435 being received into the second tube 427 while the first fluid 430 is being introduced. Suction could be applied, via the second tube, to the first fluid 435 to cause an amount of the first fluid 435 to exit the lens chamber 401 into the second tube 427. Additionally or alternatively, the first fluid 435 could exit the lens chamber 401 as a result of the introduction of the second fluid 430, e.g., due to an increase in the pressure within the lens chamber that is caused by the introduction of the second fluid 430.

Figure 4E:
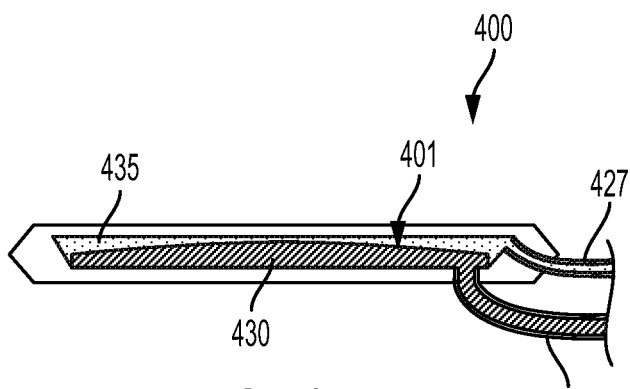
FIG. 4E is a side cross-section view of the example eye-implantable device of FIG. 4D after being filled with a fluid via the tube.
Figure 4F:
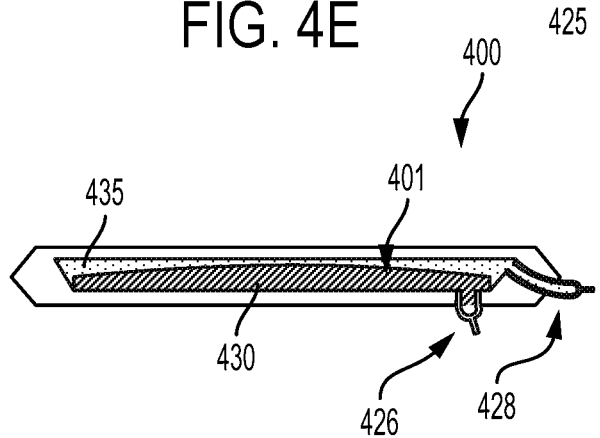
FIG. 4F is a side cross-section view of the example eye-implantable device of FIG. 4E after being the tube has been cut and crimped.

FIG. 4E shows the electrowetting lens 400 after the second fluid 430 has been introduced. Once the second fluid 430 has been provided, the tubes 425, 427 could be cut and the cut portions removed from the eye. In order to inhibit fluid flow into or out of the electrowetting lens 400 from or to the environment of the lens, the cut ends of the tubes 425, 427 could be crimped. This is shown in FIG. 4F, which illustrates the crimped and cut end of the first tube 426 and the crimped and cut end of the second tube 428. Following introduction of the second fluid 430, the electrowetting lens 400 could be operated (e.g., by applying a voltage to electrode(s) of the electrowetting lens 400) to electronically provide a controllable optical power.

In order to prevent the second fluid 430 from wetting or fouling specified surfaces within the electrowetting lens 400, to prevent dispersion of the fluids 430, 435, or to provide some other benefits, the second fluid 430 could be introduced into the lens chamber 401 after insertion of the lens into the eye, after positioning the lens at a specified location within the eye, after unfolding or unrolling the lens, or after some other processes have occurred.

Note that the tube(s) 425, 427 could be used to introduce and/or remove other fluids into/from the lens chamber 401. For example, the first tube 425 could be used to provide an amount of the first fluid 435, or of some other fluid, to rinse the lens chamber 401. Such rinsing could be performed to remove bubbles or other debris (e.g., fragments of electrode material) from the lens chamber 401, to ensure that the first fluid 435 that is present in the lens chamber 401 following such rinsing contains a specified low amount of dissolved gases, or to provide some other benefit. Additionally or alternatively, further tubes could be used to introduce and/or remove fluid(s) from the lens chamber 401 via respective fluid pathways.

Note that, while the electrowetting lenses 300, 400 shown in FIGS. 3A-F and 4A-F and/or other electrowetting lenses illustrated herein are shown as having flat top and bottom surfaces (e.g., flat top and bottom windows or lenses), electrowetting lenses as described herein could include curved internal and/or external surfaces or other curved features. Such features could be curved to provide an optical power (e.g., an optical power related to the geometry of the curved surfaces and/or features, to a difference in refractive index between materials of the electrowetting lens and an aqueous humor surrounding the electrowetting lens, and/or to some other factors).

Further, while FIGS. 3A-F and FIGS. 4A-F show the geometry of the electrowetting lenses 300, 400 remaining unchanged throughout the illustrated processes of introducing second fluids 330, 430 into the electrowetting lenses 300, 400, an electrowetting lens as described herein could be composed of flexible materials or otherwise configured to permit the geometry of the electrowetting lens to change during introduction of a fluid into the electrowetting lens. For example, an electrowetting lens could be composed of a flexible material (e.g., front and back windows of the electrowetting lens could be composed of a flexible material). A lens chamber of such an electrowetting lens could, prior to introduction of a second fluid and/or first fluid into the lens chamber, have a volume that is less than the volume of the lens chamber following introduction of such fluid(s). For example, front and back windows of such a lens chamber could be curved inward, prior to introduction of second and/or first fluids into the lens chamber. Such a lens chamber could have a decreased thickness and/or volume, relative to a lens chamber that does not change geometry upon addition of fluids into the lens chamber.

Such a decreased thickness and/or volume could permit insertion of the electrowetting lens (e.g., in a rolled or folded state) through incisions that are smaller than if the electrowetting lens did not have such a decreased thickness and/or volume owing to the inward curve of the windows (or other flexible features or elements) of the electrowetting lens. Introduction of second and/or first fluids into such an electrowetting lens could cause an increase in the volume of the electrowetting lens (e.g., by exerting an outward pressure, from inside the lens chamber, on the inward curving windows or other features of the lens chamber of the electrowetting lens), resulting in the electrowetting lens having a flat geometry or some other specified operational geometry of the electrowetting lens.

IV. EXAMPLE ELECTRONICS OF DEVICES

Figure 5:
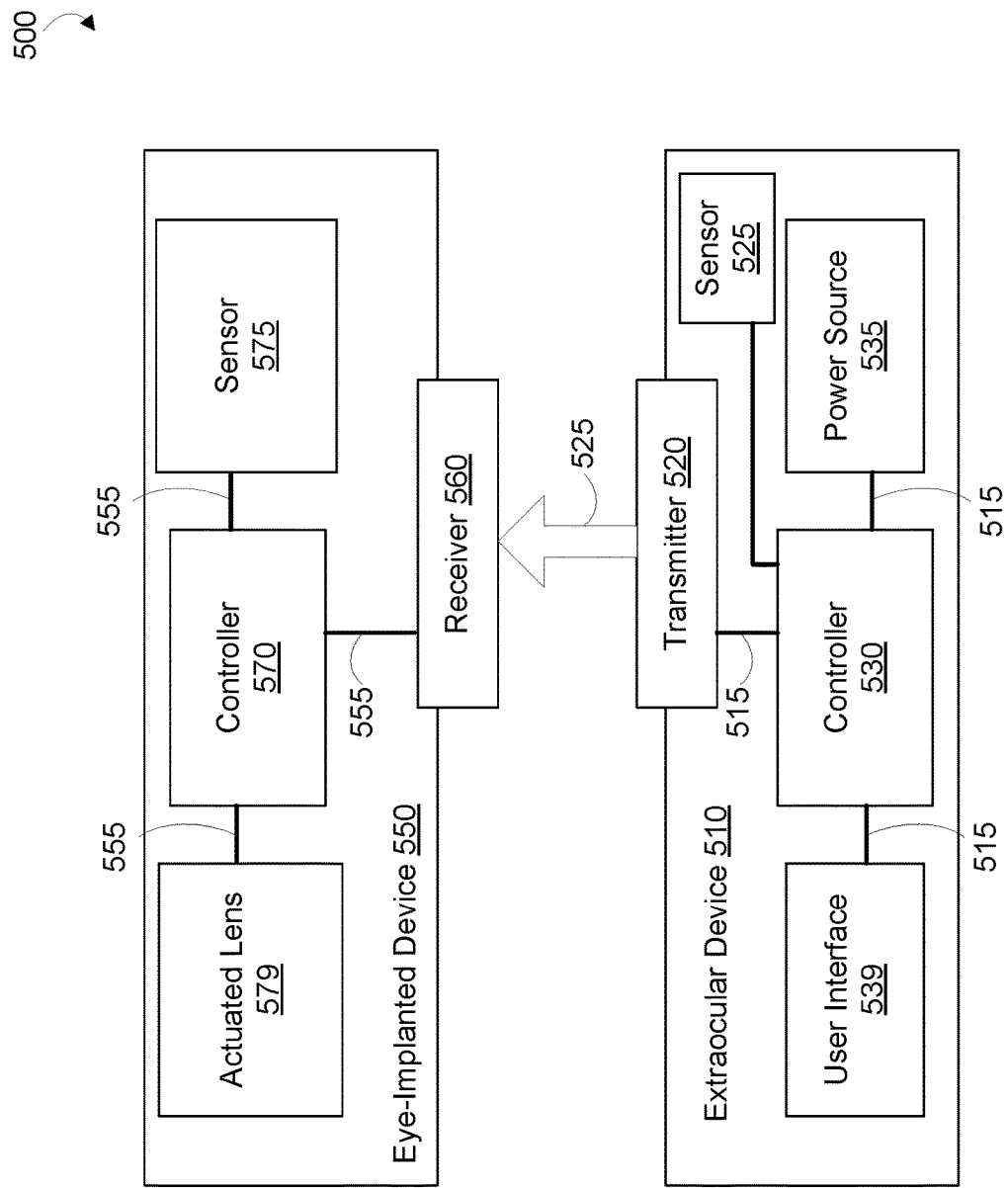
FIG. 5 is a block diagram of an example system that includes an extraocular device that can provide power to an eye-implanted device.

FIG. 5 is a block diagram of a system 500 that includes an extraocular device 510 wirelessly transmitting wireless signals 525 to an eye-implanted device 550. The wireless signals 525 may include wireless power signals to provide power to the eye-implanted device 550, control signals to control the operation of the eye-implanted device 550 (e.g., to control an optical power provided by an adjustable lens 579 of the eye-implanted device 550), or other wireless signals. The extraocular device 510 may be a body-mounted device, e.g., a contact lens, a head-mounted display, or some other type of head-mounted device. Additionally or alternatively, the extraocular device 510 may be a handheld device like a cell phone, a device incorporated into furniture, e.g., into a bed to facilitate charging of the eye-implantable device 550 while a user sleeps, or may take some other form(s). The eye-implanted device 550 is implanted on or within an eye of a user.

The extraocular device 510 includes a controller 530, user interface 539, a transmitter 520, a power source 535, and a sensor 525. The transmitter 520 can be operated to wirelessly transmit power, commands, or other signals to the eye-implanted device 550 in an eye. The transmitter 520, the controller 530, the power source 535, the user interface 539, and the sensor 525 can all be connected together via interconnects 515, e.g., via wires, cables and/or, patterns of metallic traces formed on a printed circuit board or other substrate material on which the components may be disposed. Further, the transmitter 520 could comprise metallic traces or patterns formed on such a substrate material (e.g., to form antennas, impedance matching elements, plates of capacitors, electrodes, mirrors or diffraction gratings).

The transmitter 520 can include light-emitting elements (e.g., LEDs, lasers, VCSELs), radio-frequency electromagnetic energy-transmitting elements (e.g., antennas, coils), elements configured to inject a time-varying current into tissues or fluids of a body (e.g., electrodes), or other elements configured to transmit, e.g., power from the power source 535 to the implanted device 550. The transmitter 520 could be configured to control an intensity, a phase, a frequency, a polarization, a direction, or some other properties of wireless signals transmitted from the transmitter 520 to indicate information. The transmitter 520 could be configured to provide power to the eye-implanted device 550 when the extraocular device 510 is not mounted to an eye or body of a user (e.g., when the user is sleeping in a bed such that the eye-implanted device 550 within an eye of the user is proximate to the extraocular device 510) or while the extraocular device 510 is mounted to the eye or body of the user.

The power source 535 may provide power to the extraocular device 510 to, e.g., to recharge a rechargeable battery of the power source 535 in embodiments wherein the extraocular device 510 is an eye-mountable device. The power source 535 could include a battery (e.g., single-use alkaline batteries, rechargeable lithium-polymer batteries), a solar cell, connection to a mains power source, or some other source of energy.

The sensor 525 may be configured to detect physiological properties (e.g., a pupillary diameter of an eye), environmental parameters (e.g., an ambient light level, a distance between eyes of a user and an object at which the user is looking), to detect movements of the eye and/or eyelids of a user (e.g., to detect a vergence of the eyes), or to otherwise detect physical parameters that may be relevant to the operation of the extraocular device 510 and/or the eye-implanted device 550. The user interface 539 may include displays, inputs, speakers, microphones, touchscreens, buttons, scroll wheels, or other elements to facilitate receiving information (e.g., commands) from a user and/or to provide information (e.g., a command interface, a battery status or other information about the devices 510, 550) to a user. For example, the user interface 539 may be operated to receive commands from a user related to a desired optical power of the eye-implanted device 550 and/or information about a distance a user wishes to see or some other information related to an optical power that could be desired from the eye-implanted device 550.

The eye-implanted device 550 includes a controller 570, a sensor 575, a receiver 560, and an adjustable lens 579. The adjustable lens 579 could be an electrowetting lens as described herein. The receiver 560 can be operated to receive power or other wireless signals 525 wirelessly transmitted by the transmitter 520 (e.g., from the power source 535 of the extraocular device 510). This could include receiving optical signals (e.g., via a photovoltaic cell, photodiode, or other light-sensitive elements), radio frequency electromagnetic signals (e.g., via an antenna, via a coil), an electrical current or potential in the tissues or fluids surrounding the eye-implanted device 550 (e.g., via electrodes), or receiving some other signals wirelessly transmitted from the extraocular device 510. The eye-implanted device 550 could include a capacitor, a battery, or other type of energy storage device to provide energy for use by the device 550 when power is unavailable from the other systems (e.g., when the extraocular device 510 is not mounted to or otherwise proximate to the eye-implanted device 550).

The sensor 575 is configured to detect a physiological property of the body (e.g., a pressure or force, a biopotential, a light intensity). In a particular example, the sensor 575 could be an accommodation sensor configured to detect, directly or indirectly, accommodation forces exerted on a lens capsule of the eye, e.g., by detecting a force or pressure within the lens capsule via haptics, via an elastic material disposed in the lens capsule, via detection of electrical activity of the ciliary muscles, or via some other means.

The adjustable lens 579 is operable to control an optical power that is provided to the eye by the adjustable lens 579. Operating the adjustable lens 579 to control the optical power of the lens could include applying a voltage to a liquid crystal of the lens 579, applying a voltage to electrodes of an electrowetting adjustable lens 579 or operating a pump or some other element to control a pressure and/or disposition of a fluid within the lens 579, or controlling the optical power of the lens by some other method.

The eye-implanted device 550 and/or extraocular device 510 could include additional or alternative elements, and could include more or fewer elements than those illustrated in FIG. 5. This could include the eye-implanted device 550 including elements configured to transmit wireless signals to the extraocular device 510 and the extraocular device 510 including elements configure to receive such transmitted signals. In such an example, the eye-implanted device 550 and the extraocular device 510 could additionally include a transmitter and receiver, respectively. Additionally or alternatively, the illustrated receiver 560 and transmitter 520 could be configured as transceivers to facilitate bidirectional communication and/or to share one or more elements (e.g., antennas, filters, coils, power conditioning systems) in common with other elements configured to facilitate bidirectional communication.

It is noted that the block diagram shown in FIG. 5 is described in connection with functional modules for convenience in description. However, embodiments of the extraocular device 510 and/or eye-implanted device 550 can be arranged with one or more of the functional modules ("sub-systems") implemented in a single chip, integrated circuit, and/or physical feature. That is, the functional blocks in FIG. 5 need not be implemented as separated modules. Moreover, one or more of the functional modules described in FIG. 5 can be implemented by separately packaged chips or other components electrically connected to one another. Further, note that an extraocular device and/or an eye-implantable device as described herein could include additional or alternative components to those shown in FIG. 5 (e.g., additional sensors, adjustable lenses, displays, retinal stimulator arrays, electrodes, batteries, controllers, transmitters, receivers, stimulators, etc.). For example, the power source 535 of the extraocular device 510 could be a single-use battery and the extraocular device 510 could be operated as a single-use device (e.g., operated until the battery of the power source 535 is depleted and then discarded and/or recycled).

V. EXAMPLE METHODS

Figure 6:
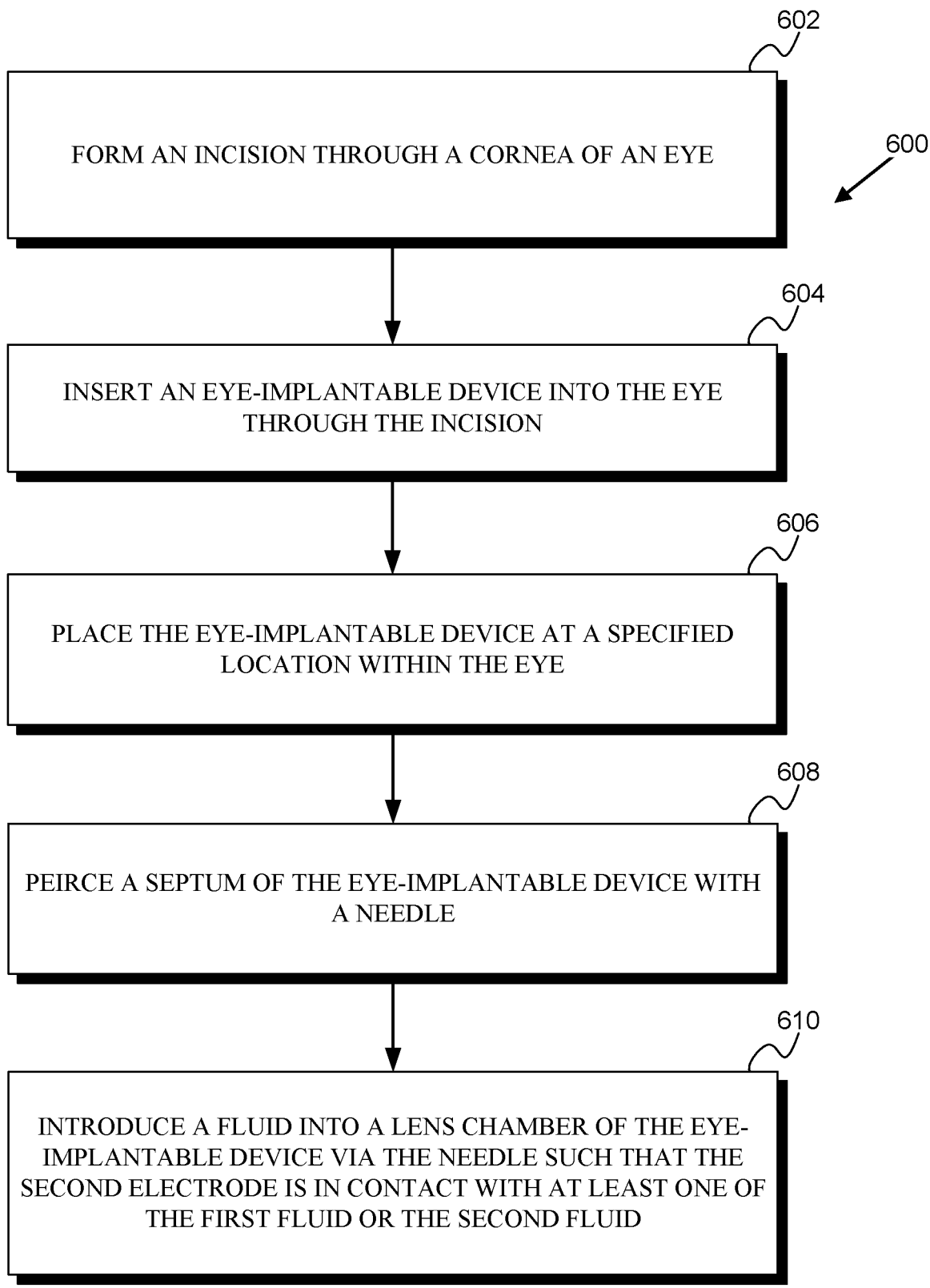
FIG. 6 is a flowchart of an example process.

FIG. 6 is a flowchart of a method 600 for implanting an eye-implantable device within a human eye. The device includes an electrowetting lens as described herein that includes (i) a lens chamber, (ii) a first fluid that is disposed within the lens chamber, (iii) a first electrode that is disposed on an internal surface of the lens chamber in contact with the first fluid, (iv) a second electrode that includes a dielectric coating and that is disposed on an internal surface of the lens chamber in contact with the first fluid, and (v) a septum that blocks a fluid pathway into the lens chamber from outside of the eye-implantable device.

The method 600 includes forming an incision through the cornea of an eye (602). This could include operating a scalpel, a laser, a diamond blade, a metal blade, or some other instruments to create an incision through the cornea. The incision could be created by creating multiple separate cuts or incisions into the cornea. For example, a first cut could be made perpendicular to the surface of the sclera, and one or more subsequent cuts could be made at other angles (e.g., tangential angles) relative to the sclera. The incision could be formed to be water-tight, to cause a minimum of astigmatism, or to satisfy some other considerations. The formation of the incision could be accompanied by mechanical stabilization of the eye (e.g., using fixation rings, forceps, or other means), administration of topical or global anesthesia, or some other steps. The formed incision could have a length or other dimension within some specified range; e.g., the incision could be less than 4 millimeters long, or less than 2 millimeters long.

The method 600 includes inserting the eye-implantable device into the eye through the incision (604). This could include using forceps or some other means to insert the eye-implantable device through the incision. Additionally or alternatively, the eye-implantable device could include tabs, rods, or other features to facilitate such insertion. Such features could be later removed from the eye-implantable device (e.g., by cutting, crimping, laser cutting, or some other means) or could remain as part of the eye-implantable device following implantation. The eye-implantable device could be inserted as multiple components (e.g., multiple components connected via one or more cables or other connecting means).

The method 600 further includes placing the eye-implantable device at a specified location within the eye (606). As noted above for insertion of the eye-implantable device through the incision, this could include using instruments to manipulate and position the eye-implantable device and/or using tabs, rods, or other features of the eye-implantable device. Placing the eye-implantable device at the specified location could include inserting the device through additional incisions or other surgically formed features of the eye (e.g., an incision through the iris, through a hole formed in the lens capsule of the eye) and/or through natural features of the eye (e.g., through the pupil of the iris). The specified location could be within the lens capsule, in the anterior capsule, in the posterior capsule, in the vitreous humor, or in some other location of the eye. Placing the eye-implantable device at the specified location could include manipulating haptics or other features of the device and/or additional implanted elements in order to secure the device at the specified location, to facilitate interactions between the device and the eye (e.g., to facilitate detection of accommodation forces applied to the lens capsule of the eye), or to provide some other benefit. Placing the eye-implantable device at the specified location could include assembling multiple different elements of the device together, e.g., assembling an electrowetting lens together with an electronics module to form the eye-implantable device.

The method 600 further includes piercing the septum with a needle (608). This could include manipulating the electrowetting lens to secure the electrowetting lens while piercing the septum. Piercing the septum could include aligning the needle with fiducials or other features of the electrowetting lens and/or of the eye-implantable device. For example, the needle could be part of an instrument that is configured to clamp or otherwise secure the electrowetting lens at a specified location relative to the instrument (e.g., using fiducials, tabs, or other alignment features of the eye-implantable device and/or of the instrument) and subsequently to pierce the septum using the needle. The needle could be used to pierce the septum manually (e.g., the needle could be part of a syringe held by a surgeon) and/or an instrument could include one or more motors, pistons, or other elements configured to use the needle to pierce the septum.

The method 600 further includes introducing a second fluid into the lens chamber via the needle such that the second electrode is in contact with at least one of the first fluid or the second fluid (610). The second fluid is immiscible with the first fluid and has a refractive index that differs from a refractive index of the first fluid. Introducing the second fluid into the lens chamber could include operating a syringe to inject the second fluid into the lens chamber via the needle. Additionally or alternatively, one or more pumps, reservoirs, microfluidic elements, or other devices or systems could be used to introduce the second fluid via the needle, e.g., by applying a specified pressure to the second fluid, by introducing the second fluid at a specified flow rate, or by introducing the second fluid according to some other consideration.

Figure 7:
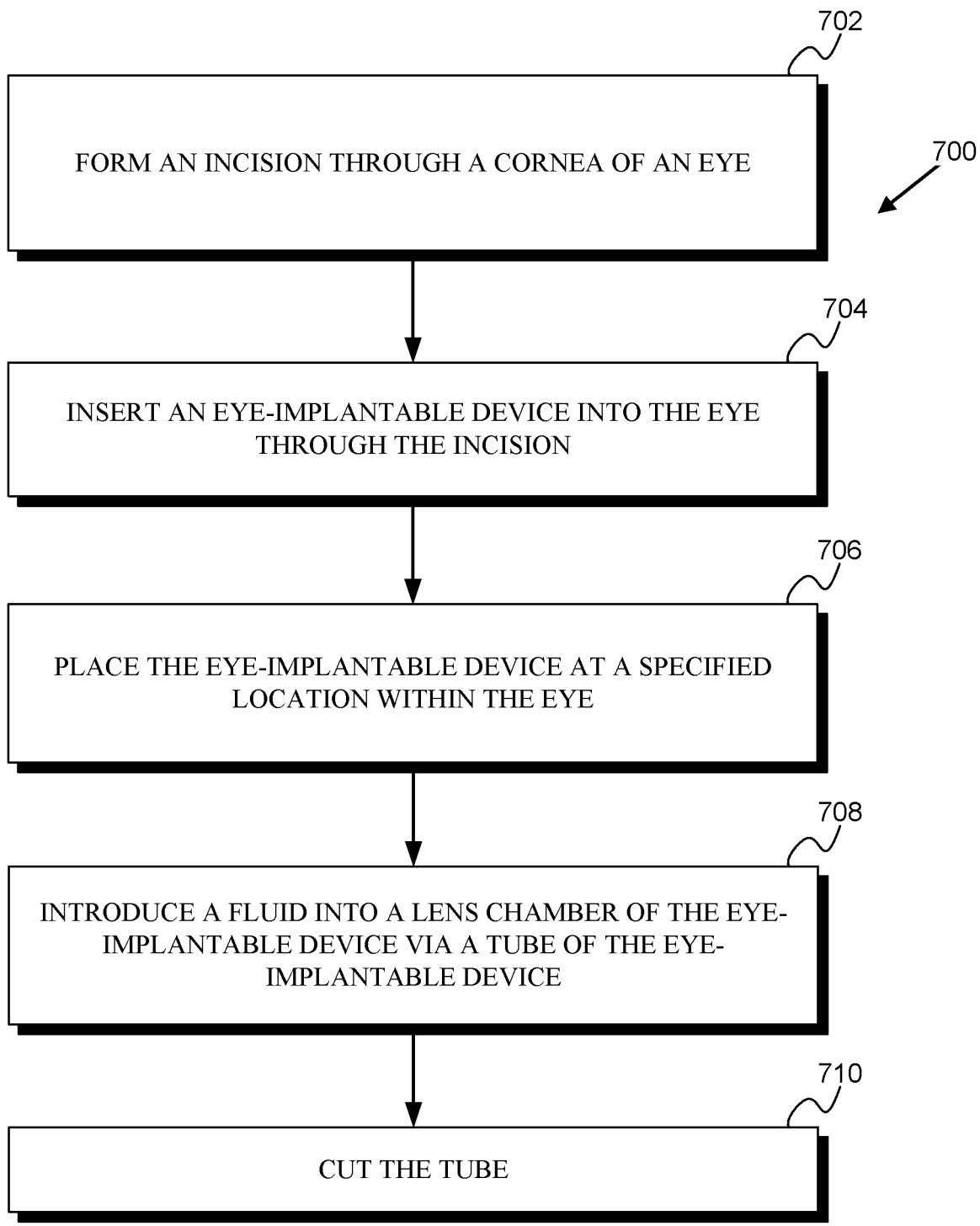
FIG. 7 is a flowchart of an example process.

FIG. 7 is a flowchart of a method 700 for implanting an eye-implantable device within a human eye. The device includes an electrowetting lens as described herein that includes (i) a lens chamber, (ii) a first fluid that is disposed within the lens chamber, (iii) a first electrode that is disposed on an internal surface of the lens chamber in contact with the first fluid, (iv) a second electrode that includes a dielectric coating and that is disposed on an internal surface of the lens chamber in contact with the first fluid, and (v) a tube that protrudes from the eye-implantable device and that provides at least a portion of a fluid pathway into the lens chamber from outside of the eye-implantable device.

The method 700 includes forming an incision through the cornea of an eye (702); inserting the eye-implantable device into the eye through the incision (704); and placing the eye-implantable device at a specified location within the eye (706). These elements could be performed in as described above in connection with method 600 or in some other manner. For example, an instrument used to insert the eye-implantable device could be configured to receive the tube of the eye-implantable device and/or to maintain a connection between the tube and a source of fluid(s), suction, or some other system(s).

The method 700 further includes introducing a second fluid into the lens chamber via the tube such that the second electrode is in contact with at least one of the first fluid or the second fluid (708). The second fluid is immiscible with the first fluid and has a refractive index that differs from a refractive index of the first fluid. Introducing the second fluid into the lens chamber could include operating a syringe to inject the second fluid into the lens chamber via the tube. Additionally or alternatively, one or more pumps, reservoirs, microfluidic elements, or other devices or systems could be used to introduce the second fluid via the tube, e.g., by applying a specified pressure to the second fluid, by introducing the second fluid at a specified flow rate, or by introducing the second fluid according to some other consideration.

The method 700 further includes cutting the tube (710). This could include applying mechanical forces (e.g., using a scalpel, scissors, or other bladed implements), ultrasonic energy, light energy (e.g., a laser), or some other energies or forces to cut the tube. In some examples, the tube could be crimped to inhibit fluid flow through the tube at the same time that the tube is cut, e.g., by application of ultrasonic energy to seal the tube together and to section the tube. The tube could include features to facilitate cutting and/or sectioning the tube at one or more specified locations. For example, the tube could include a material configured to preferentially absorb light or acoustical energy at a particular frequency. In another example, the tube could be scored or include other formed features that facilitate sectioning of the tube, e.g., by application of shear forces or tensions to the tube.

Method 600 or method 700 could include additional steps or elements in addition to those depicted in FIGS. 6 and 7. For example, the methods 600, 700 could include adding or removing other materials or fluids to or from a lens chamber of an eye-implantable device, e.g., adding or removing an amount of the first fluid. This could be performed using one or more needles, one or more tubes connected between the device and external systems, or via some other method. For example, the lens chamber could be rinsed by introducing an amount of the first fluid into the lens chamber, e.g., via the needle, via one or more further needles, via the tube, via one or more further tubes, or via some other means. Additionally or alternatively, an amount of the first fluid could be removed from the lens chamber, e.g., by applying suction via the needle, tube, or other fluid transfer means. The methods 600, 700 could include removing gases from one or both of the first or second fluids prior to introducing such fluids into the lens chamber.

The methods 600, 700 could include retracting the needle, crimping the tube, retracting a sectioned portion of the tube, and/or performing some further assembly or other processes to an eye-implantable device. For example, the eye-implantable device could include a tube that protrudes from the device and that provides a fluid pathway into the lens chamber (e.g., to facilitate the exit of an amount of the first fluid from the lens chamber when the second fluid is introduced). The methods 600, 700 could include crimping, cutting, or otherwise manipulating such a tube, e.g., to inhibit fluid flow through the tube. Crimping such a tube could include applying a mechanical, acoustical, electromagnetic, or thermal force to induce some change in the material of the tube, e.g., to melt the tube, to cause opposite walls of the tube to chemically interact, to cause a material in the tube to undergo photopolymerization, or to cause some other process. Additionally or alternatively, a staple or other means could be applied to the tube to crimp the tube.

The methods 600, 700 could include further surgical manipulations of the eye, e.g., the formation of a hole in the lens capsule and/or the removal of the crystalline lens, the removal of a previously implanted device (e.g., a static IOL). The methods 600, 700 could include programming and/or testing an eye-implantable device. In some examples, the eye-implantable device could be rolled, folded, or otherwise manipulated to reduce one or more dimensions of the device (e.g., in order to facilitate insertion of the device through a smaller incision) and the methods 600, 700 could include unrolling, unfolding, or otherwise manipulating the eye-implantable device subsequent to inserting the device through the incision. In some examples, the eye-implantable device could be implanted through the sclera or via some other route, and the methods 600, 700 could include forming alternative incisions (e.g., through the sclera) and inserting the device through such alternative incisions.

VI. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. An eye-implantable device comprising:
   an electrowetting lens, wherein the electrowetting lens comprises:
   a lens chamber;
   a polymeric material, wherein the polymeric material at least partially encloses the lens chamber;
   a first electrode, wherein the first electrode is disposed on a first internal surface of the polymeric material;
   a second electrode, wherein the second electrode is disposed on a second internal surface of the polymeric material, wherein the second electrode comprises a dielectric coating; and
   a septum, wherein the septum blocks a fluid pathway into the lens chamber from outside of the eye-implantable device, such that the septum can be penetrated and a first fluid introduced into the lens chamber through the fluid pathway from outside of the eye-implantable device such that the first fluid contacts the second electrode but not the first electrode.

2. The eye-implantable device of claim 1, further comprising a second fluid, wherein the second fluid is disposed in the lens chamber, wherein the first electrode and the second electrode are in contact with the second fluid.

3. The eye-implantable device of claim 2, wherein the polymeric material is flexible such that the electrowetting lens can be folded.

4. The eye-implantable device of claim 2, wherein the fluid pathway comprises a channel between the septum and the lens chamber.

5. The eye-implantable device of claim 2, wherein the septum comprises a silicone rubber.

6. An eye-implantable device comprising:
   an electrowetting lens, wherein the electrowetting lens comprises:
   a lens chamber;
   a polymeric material, wherein the polymeric material at least partially encloses the lens chamber;
   a first electrode, wherein the first electrode is disposed on a first internal surface of the polymeric material;
   a second electrode, wherein the second electrode is disposed on a second internal surface of the polymeric material, wherein the second electrode comprises a dielectric coating; and
   a tube that protrudes from the eye-implantable device, wherein the tube provides at least a portion of a fluid pathway into the lens chamber from outside of the eye-implantable device, such that a first fluid can be introduced into the lens chamber through the tube from outside of the eye-implantable device such that the first fluid contacts the second electrode but not the first electrode.

7. The eye-implantable device of claim 6, further comprising a second fluid, wherein the second fluid is disposed in the lens chamber, wherein the first electrode and the second electrode are in contact with the second fluid.

8. The eye-implantable device of claim 7, wherein the polymeric material is flexible such that the electrowetting lens can be folded.

9. The eye-implantable device of claim 7, wherein the tube includes a crimpable portion, and wherein crimping the crimpable portion of the tube inhibits fluid flow out of the eye-implantable device via the tube.

10. A method comprising:
    forming an incision through a cornea of an eye;
    inserting an eye-implantable device into the eye through the incision, wherein the eye-implantable device comprises:
    an electrowetting lens, wherein the electrowetting lens comprises: (i) a lens chamber, (ii) a polymeric material, wherein the polymeric material at least partially encloses the lens chamber, (iii) a first electrode, wherein the first electrode is disposed on a first internal surface of the polymeric material, (iv) a second electrode, wherein the second electrode is disposed on a second internal surface of the polymeric material, wherein the second electrode comprises a dielectric coating, and (v) a septum, wherein the septum blocks a fluid pathway into the lens chamber of the electrowetting lens from outside of the eye-implantable device;
    placing the eye-implantable device at a specified location within the eye;
    piercing the septum with a needle; and
    introducing a second fluid into the lens chamber via the needle when a first fluid is already present in the lens chamber such that the second fluid contacts the second electrode but not the first electrode, wherein the second fluid is immiscible with the first fluid, and wherein a refractive index of the second fluid differs from a refractive index of the first fluid.

11. The method of claim 10, wherein the electrowetting lens is flexible such that the electrowetting lens can be folded, wherein inserting an eye-implantable device into the eye through the incision comprises inserting the eye-implantable device in a folded state, and further comprising:
    subsequent to inserting the eye-implantable device into the eye through the incision, unfolding the electrowetting lens of the eye-implantable device.

12. The method of claim 11, wherein the incision is less than 4 millimeters long.

13. The method of claim 10, further comprising rinsing the lens chamber, wherein rinsing the lens chamber comprises introducing an amount of the first fluid into the lens chamber via the needle.

14. The method of claim 10, wherein the eye-implantable device further comprises a tube that protrudes from the eye-implantable device, wherein the tube provides at least a portion of the fluid pathway into the lens chamber from outside of the eye-implantable device, and wherein the method further comprises:

crimping the tube, wherein crimping the tube inhibits fluid flow out of the eye-implantable device via the tube.

15. A method comprising:

forming an incision through a cornea of an eye;

inserting an eye-implantable device into the eye through the incision, wherein the eye-implantable device comprises:

an electrowetting lens, wherein the electrowetting lens comprises: (i) a lens chamber, (ii) a polymeric material, wherein the polymeric material at least partially encloses the lens chamber, (iii) a first electrode, wherein the first electrode is disposed on a first internal surface of the polymeric material, (iv) a second electrode, wherein the second electrode is disposed on a second internal surface of the polymeric material, wherein the second electrode comprises a dielectric coating, and (v) a tube that protrudes from the eye-implantable device, wherein the tube provides at least a portion of a fluid pathway into the lens chamber of the electrowetting lens from outside of the eye-implantable device;

placing the eye-implantable device at a specified location within the eye;

introducing a second fluid into the lens chamber via the tube when a first fluid is already present in the lens chamber such that the second fluid contacts the second electrode but not the first electrode, wherein the second fluid is immiscible with the first fluid, and wherein a refractive index of the second fluid differs from a refractive index of the first fluid; and cutting the tube.

16. The method of claim 15, wherein the electrowetting lens is flexible such that the electrowetting lens can be folded, wherein inserting an eye-implantable device into the eye through the incision comprises inserting the eye-implantable device in a folded state, and further comprising:

subsequent to inserting the eye-implantable device into the eye through the incision, unfolding the electrowetting lens of the eye-implantable device.

17. The method of claim 16, wherein the incision is less than 4 millimeters long.

18. The method of claim 15, further comprising crimping the tube, wherein crimping the tube inhibits fluid flow out of the eye-implantable device via the tube.

19. The method of claim 15, further comprising rinsing the lens chamber, wherein rinsing the lens chamber comprises introducing an amount of the first fluid into the lens chamber via the tube.

20. The method of claim 15, wherein the eye-implantable device further comprises a further tube that protrudes from the eye-implantable device, wherein the further tube provides at least a portion of a further fluid pathway between the lens chamber and the outside of the eye-implantable device, wherein the further tube receives an amount of the first fluid from the lens chamber when the second fluid is introduced into the lens chamber via the tube, and wherein the method further comprises:

crimping the further tube, wherein crimping the further tube inhibits fluid flow out of the eye-implantable device via the further tube.

* * * * *